(12) United States Patent
Doguet et al.

(10) Patent No.: US 11,951,305 B2
(45) Date of Patent: Apr. 9, 2024

(54) ACTIVE IMPLANTABLE STIMULATING DEVICE FOR USE WITH AN MRI-DEVICE

(71) Applicant: Synergia Medical, Mont-Saint-Guibert (BE)

(72) Inventors: Pascal Doguet, Mont-Saint-Guibert (BE); Aurore Nieuwenhuys, Mont-Saint-Guibert (BE); Yohan Botquin, Mont-Saint-Guibert (BE); Jérôme Garnier, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 0 days.

(21) Appl. No.: 17/920,419

(22) PCT Filed: May 4, 2020

(86) PCT No.: PCT/EP2020/062331
§ 371 (c)(1),
(2) Date: Oct. 21, 2022

(87) PCT Pub. No.: WO2021/223839
PCT Pub. Date: Nov. 11, 2021

(65) Prior Publication Data
US 2023/0147433 A1 May 11, 2023

(51) Int. Cl.
*A61N 1/372* (2006.01)
*A61B 5/00* (2006.01)
(Continued)

(52) U.S. Cl.
CPC .............. *A61N 1/08* (2013.01); *A61B 5/0017* (2013.01); *A61B 5/294* (2021.01); *A61B 5/6822* (2013.01);
(Continued)

(58) Field of Classification Search
CPC ...... A61N 1/375–3754; A61N 1/37211; A61N 1/37217; A61N 1/086; A61N 1/0622
See application file for complete search history.

(56) References Cited

U.S. PATENT DOCUMENTS

| 4,694,836 A | 9/1987 | Buikman et al. |
| 7,974,697 B2 | 7/2011 | Maschino et al. |

(Continued)

FOREIGN PATENT DOCUMENTS

| WO | 2010148324 A1 | 12/2010 |
| WO | 2021139887 A1 | 7/2021 |

OTHER PUBLICATIONS

Int'l Search Report for PCT/EP2020/062331, dated Jan. 20, 2021.
(Continued)

*Primary Examiner* — George R Evanisko
(74) *Attorney, Agent, or Firm* — MaxGoLaw PLLC

(57) ABSTRACT

A kit-of-parts for visualizing by a magnetic resonance imaging (MRI) technique including a functional magnetic resonance imaging (fMRI) technique, regions of a central nervous system of a patient having an implanted active implantable medical device (AIMD) is provided. The kit-of-parts is provided and includes:
the AIMD, which can be used exposed to the electromagnetic conditions for MR-images acquisition,
an external processing unit for controlling the AIMD,
an optical communication lead for establishing a two-way optical communication between the AIMD and
an external communication unit which is controlled by the external processing unit.

A patient having an implanted AIMD can be treated in a conventional MR-device for imaging, e.g., a brain region. The other elements of the kit-of-parts allow controlling the (Continued)

functions of the AIMD and following any effects of a stimulation on the brain region thus imaged.

10 Claims, 8 Drawing Sheets

(51) Int. Cl.
  *A61B 5/294*    (2021.01)
  *A61N 1/08*     (2006.01)
(52) U.S. Cl.
  CPC ..... *A61N 1/37223* (2013.01); *A61N 1/37247* (2013.01)

(56) References Cited

U.S. PATENT DOCUMENTS

| | | |
|---|---|---|
| 8,233,985 B2 | 7/2012 | Bulkes et al. |
| 8,332,037 B2 * | 12/2012 | Imran ................ A61N 1/36064 607/36 |
| 9,901,284 B2 | 2/2018 | Olsen et al. |
| 10,350,424 B2 | 7/2019 | Doguet |
| 10,507,330 B2 | 12/2019 | Doguet et al. |
| 10,974,066 B2 | 4/2021 | Doguet et al. |
| 11,052,260 B2 | 7/2021 | Doguet et al. |
| 11,318,301 B2 | 5/2022 | Doguet et al. |
| 2005/0070972 A1 | 3/2005 | Wahlstrand et al. |
| 2005/0177200 A1 | 8/2005 | George et al. |
| 2012/0059442 A1 | 3/2012 | Cox et al. |
| 2015/0080982 A1 * | 3/2015 | Van Funderburk ......................... A61N 1/37247 607/59 |
| 2022/0054841 A1 | 2/2022 | Doguet et al. |

OTHER PUBLICATIONS

Lomarev, et al., "Vagus nerve stimulation (VNS) synchronized BOLD fMRI suggests that VNS in depressed adults has frequency/dose dependent effects", Journal of Psych. Research, 36 (2002), pp. 219-227.

* cited by examiner

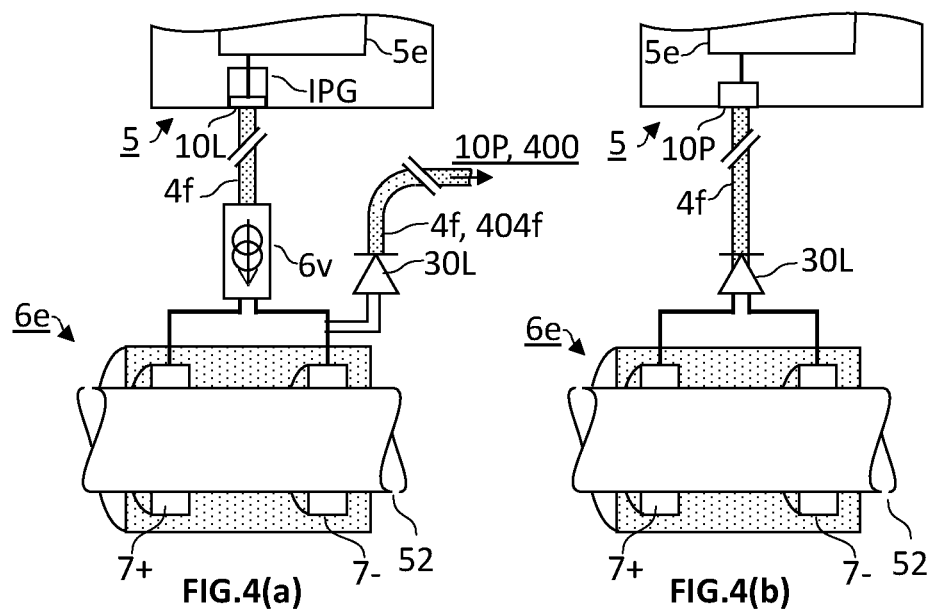
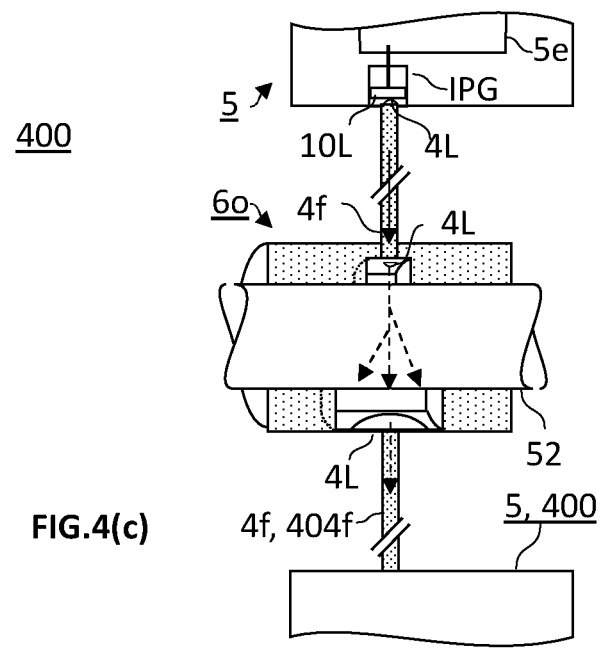

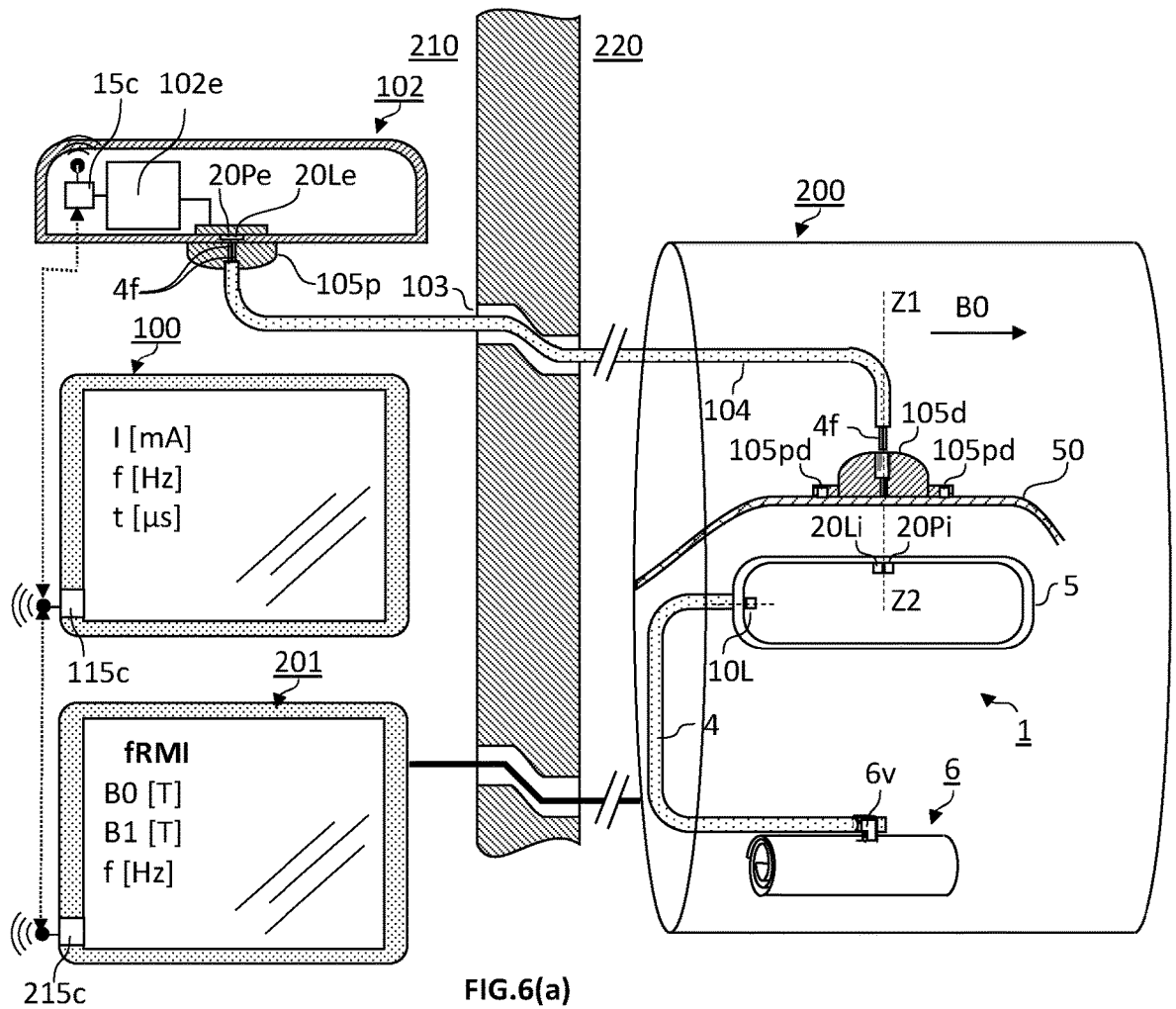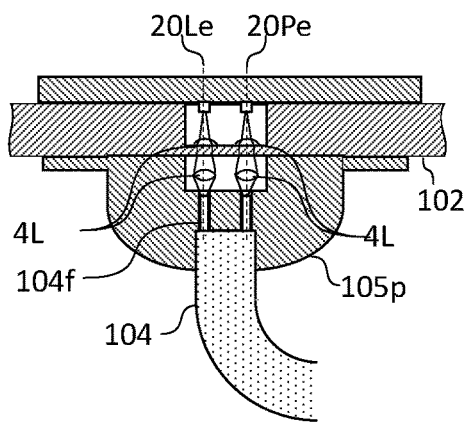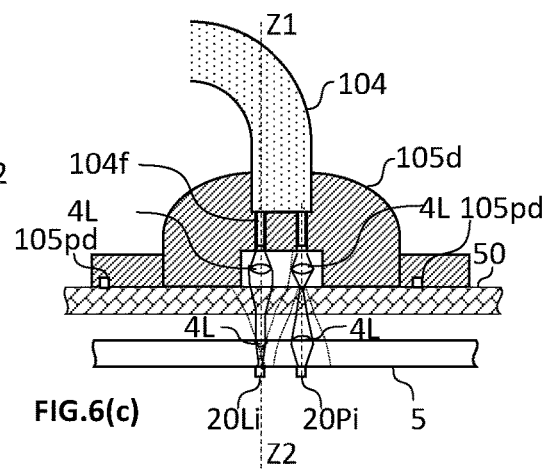
FIG.6(a)
FIG.6(b)          FIG.6(c)

ACTIVE IMPLANTABLE STIMULATING DEVICE FOR USE WITH AN MRI-DEVICE

TECHNICAL FIELD

The present invention is in the field of electronic active implantable medical devices (AIMD) for implantation in a body for medical treatment of a patient. The AIMD of the present invention is suitable for use in imaging and characterizing the patient in a magnetic resonance (MR-) device, such as by MR-imaging (MRI) or functional MR-imaging (fMRI). In particular, the present invention concerns a kit-of-parts comprising such an AIMD, an external processing unit, and optical fibres for establishing a communication between the AIMD and the external processing unit. The AIMD of the kit-of-parts of the present invention is fully operational as an implant and can be controlled when implanted in a patient and when said patient is exposed to an oscillating magnetic field and/or electric field used in MR-devices.

The present invention has the advantage not only of allowing MR-imaging of a patient implanted with such AIMD, but also and above all of allowing the visualization of the effects on the brain activity of various controlled treatment parameters of the AIMD by MRI or fMRI.

BACKGROUND OF THE INVENTION

Active implantable medical devices (AIMD) have been used for decades for treating a number of disorders, in particular neurological disorders. In its simplest form, an AIMD consists of an encapsulation unit enclosing electronic components and can support sensors for monitoring biomarkers of a patient. The sensors can either be lodged in an interior of the encapsulation unit, or fixed to an outer surface of the encapsulation unit, or can be separate from the encapsulation unit, coupled thereto by a lead for transferring data collected by the sensors to the electronic components lodged within the encapsulation unit.

A major type of AIMD's, however, consists of neurostimulators which, instead of, or additionally to monitoring biomarkers, are configured for delivering electrical pulses to a tissue such as a nerve or a muscle for diagnosing or treating a number of disorders such as Parkinson's disease, epilepsy, chronic pain, motor disorders, and many other applications. Depending on the tissue to be treated, the type of electrodes used, and the distance between electrodes, the voltage required between implanted electrodes can be of the order of 15V±5V. Such voltage requires an implanted pulse generator (IPG) and a source of electric power (such as a battery) of such dimensions that electric stimulating implants are generally formed of three separate components: on the one hand, the electrodes which are implanted directly onto the tissue to be treated and, on the other hand, the implanted pulse generator (IPG), electronics for controlling the IPG, and battery, of larger dimensions, are enclosed in the encapsulation unit, which can be implanted at various locations in the body depending upon the application but most often in the subclavian region, the lower abdominal area or gluteal region. The energy pulses are transferred from the IPG to the tissue interaction unit via an energy transfer lead, forming the third component, and which can be formed of conductive wires or optical fibres coupled to a photovoltaic cell for transforming optical energy into electrical energy, as described, e.g., in EP311383861. In case of conductive wires, the IPG emits electric pulses, and in case of optical fibres, the IPG emits optical pulses.

In recent years, treatment of tissues with optical energy has shown encouraging potential for the treatment of disorders, either to support the field of optogenetics or using the direct effect of infrared or other wavelengths of light. For such light treatments of a tissue, a so-called optrode can be used. An optrode can be a light emitter focusing a light beam onto a precise area of a tissue, or it can be a light sensor, sensing a reflected, transmitted, or scattered light beam emitted by a light emitter.

Patients carrying an AIMD implanted in their body must be careful before undergoing a magnetic resonance imaging session in an MR-device, as the various magnetic fields required for acquiring an image can interact in various ways with the AIMD. For example, any component of the AIMD made of a ferromagnetic material can move as they are attracted by the strong static magnetic field (B0) applied in an MR-device. The RF-field (B1) can generate burns in the tissues surrounding the AIMD caused by strong induced electric currents flowing along conductive components. The strong fields can also interact with the electronics of the AIMD and either destroy some components or send undesired energy pulses to the tissues. AIMD's which can be used switched off in a MR-device without causing injuries to the patient it is implanted in have been proposed in the art.

US20120059442 proposes to provide a lead coupling an electrode unit to an encapsulation unit, with a plurality of electrodes being electrically coupled to a plurality of terminals through a plurality of conductors within a lead body of the lead. The plurality of electrodes are arranged such that adjacent pairs of electrodes are capacitively coupled through a first surface of a first electrode of the respective pair and a respective second surface of a second electrode of the respective pair to substantially block current flow between adjacent electrodes at stimulation frequencies and to substantially pass current between adjacent electrodes at MRI frequencies.

US20050070972 describes an AIMD comprising an encapsulation unit, a conductive stimulation lead having a first proximal end, and a distal electrode electrically coupled to a first distal end of the conductive stimulation lead. The AIMD further comprises a lead extension having a second proximal end electrically coupled to the encapsulation unit and having a second distal end electrically coupled to the first proximal end. A shunt is electrically coupled to the first proximal end for diverting RF energy from the lead.

U.S. Pat. No. 8,233,985 describes an AIMD provided with an antenna module, that is compatible with a magnetic resonance imaging scanner for the purpose of diagnostic quality imaging. The antenna module comprises an electrically non-conducting, biocompatible, and electromagnetically transparent enclosure with inductive antenna wires looping around an inside surface. An electronic module is enclosed in an electromagnetic shield inside the enclosure to minimize the electromagnetic interference.

When AIMD's which will not cause injuries to a patient undergoing an MRI in an MR-device can be found on the market, most of them, must be switched off during an imaging session to avoid ruining electronic components or sending erroneous and potentially dangerous pulses to the tissues.

Neurostimulation has shown beneficial clinical effects in treating diseases like epilepsy, but little is known on the exact mechanisms involved. The IPG's in neurostimulators are generally configured for continuously emitting trains of pulses of given parameters, including frequency, duration, pulse width, and intensity, separated from one another by predefined off-time intervals, during the whole period of the treatment. The determination of the values of the foregoing parameters of the pulses the AIMD is programmed to deliver to a tissue is empirical, by trial and error, based mostly on the feedback of the patients and not on a reliable diagnostic tool. Magnetic resonance imaging (MRI) and, more specifically functional magnetic resonance imaging (fMRI) would be excellent candidates for optimizing the values of the parameters of the pulses to each given patient, by tracking the effects observed in the patient to a given stimulation pattern as a function of the foregoing parameters.

U.S. Pat. No. 7,974,697 describes an adaptive stimulation process using medical imaging feedback data for affecting an operation of an implantable medical device. A stimulation signal is applied, and MR-imaging data is acquired that is indicative of whether the target portion of the brain is modulated as a result of the first stimulation signal. If no modulation is observed, a second stimulation signal is applied, and so on until a modulation is observed. In this process, the stimulations and MR-image acquisitions are activated sequentially.

Similarly, US20050177200 describes sequential neurostimulation of patients with major depressions, followed by blood-oxygen-level-dependent imaging (BOLD) by fMRI after stimulation. The type of AIMD used in the method, is not defined.

Lomarev et al., Journal of Psychiatric Research, 36 (2002) 219-227, measured blood-oxygen-level-dependent imaging (BOLD) by fMRI during stimulation by an implanted neurostimulator of patients suffering of treatment resistant depression. This study allowed a mapping of regions of the brain reacting to some stimulation parameters. The static magnetic field (B0) applied during fMRI sessions was, however, restricted to 1.5 T only. No explanation is given why higher static magnetic fields, yielding a higher resolution, were not applied. The authors do not define the models of AIMD's used and had to discard a third of the patient panel because of AIMD's being incompatible with the MR-imaging session, The paper does not mention any means to check whether the AIMD's keep functioning as programmed during the fMRI sessions.

U.S. Pat. No. 9,901,284 describes a system comprising a MR-device, an AIMD and a processor configured to generate an indication that the AIMD has or will cycle in an electrical stimulation therapy while the patient is in the MR-device or is being imaged by the MRI unit. An MRI scan of the patient is initiated based on the indication. The AIMD is an electrical stimulating implant comprising an encapsulation unit coupled to a pair of electrodes via electric leads. However, little information on the structure of the components of the AIMD is available in this document. Communication between the processor and the AIMD is carried out by wireless telemetry, e.g., by radio frequency (RF) communication or proximal inductive interaction with the AIMD.

Therefore, there remains a need for AIMD's which can be used and activated during MRI and fMRI sessions, with static magnetic fields (B0) of any magnitude, such as 1.5, 3, or even 7 T, with a feedback system ensuring that the stimulation pulses generated during MR-image acquisition are as programmed in spite of the intense electromagnetic fields. This would open the door to a rigorous study of the mechanisms of neurostimulation responsible for the beneficial clinical effects observed.

The present invention proposes an AIMD which can safely be used and operated during MR-imaging conditions. It also proposes a kit-of-parts including processing units and communication means which allow a safe, reliable and reproducible control of the functions of the AIMD exposed to MR-mage acquisition conditions. A system is proposed which makes analysis possible of the influence of various stimulation parameters on the clinical effects of neurostimulation on different diseases, including epilepsy. These and more advantages of the present invention are described in continuation.

SUMMARY OF THE INVENTION

The present invention is defined in the appended independent claims. Preferred embodiments are defined in the dependent claims. In particular, the present invention concerns a kit-of-parts for visualizing by a magnetic resonance imaging (MRI) technique including a functional magnetic resonance imaging (fMRI) technique, regions of a central nervous system of a patient having an implanted active implantable medical device (AIMD), The kit-of-parts comprises:
    the AIMD,
    an external processing unit,
    an external communication unit, and
    an optical communication lead.
The AIMD comprises an encapsulation unit defining an inner space (Vi) sealingly separated from an outer environment by walls defined by an inner surface defining the boundaries of the inner space. The walls of the encapsulation unit are made of a non-metallic material, preferably selected among ceramic and polymers, such as fused silica or a spinel, wherein the inner space contains:
    an implanted source of communication light and an implanted communication photodetector facing a portion of wall having a given transmittance to wavelength selected within the range comprised between 380 nm and 5 µm, preferably between 600 nm and 2200 nm for optical communication with an exterior of the body; the portion of wall preferably has a transmittance to a wavelength of 850 nm at room temperature of at least 75%, more preferably of at least 85%,
    an electronic circuit for controlling the implanted source of communication light and the implanted communication photodetector, thus ensuring communication with the exterior.
The external processing unit comprises a user interface configured for entering parameters and commands, and for displaying information. The external processing unit controls the functions of the AIMD and communicates therewith via the external communication unit.

The external communication unit is in communication with the external processing unit and comprises an external source of communication light, an external photodetector, and an electronic circuit configured for,
    controlling the external source of communication light to emit signals representative of the parameters and commands entered in the external processing unit and received by the implanted communication photodetector, and
    transferring to the external processing unit information representative of optical communication signals emitted by the implanted source of communication light (20Li) and received by the external photodetector.
The optical communication lead comprises an optical fibre for establishing an optical communication between,
    on the one hand, the implanted source of communication light of the AIMD and the external communication photodetector of the external communication unit (102), and on the other hand, the external source of communication light of the external communication unit, and the implanted photodetector of the AIMD, The optical communication lead establishes a two way remote optical communication between the external processing unit and the AIMD, from the external processing unit to the AIMD to control the latter and from the AIMD to the external processing unit to provide feedback information to the external processing unit, such as control signals confirming the good functioning of the AIMD, or measurements of biomarkers.

In a preferred embodiment, the optical communication lead (104) comprises at least two optical fibres. IN this embodiment each optical fibre comprises, a proximal end inserted in a proximal interface device which is coupled to the external communication unit such that the optical fibres are optimally aligned with the external communication photodetector and external source of communication light of the external communication unit, and a distal end inserted in a distal interface device, wherein for aligning the distal ends of the optical fibres with the implanted source of communication light and the implanted communication photodetector, the distal interface device preferably comprises a number, N>2, of centring photodetectors forming a polygon of N edges, configured for receiving and detecting an intensity of a light beam emitted by the implanted source of communication light when the distal interface device is laid on a skin of the patient over an approximate position of the encapsulation unit with the N centring photodetectors facing towards the skin, wherein micro-optical elements including one or more of anyone of lenses, collimators, diffusors, polarizers, or filters, are preferably provided, which are configured for reshaping a beam of light propagating in both directions from or towards the proximal end and/or distal end of each of the optical fibres.

In a preferred embodiment, the AIMD comprises three main components, the encapsulation unit, a tissue interaction unit, and an energy transfer lead. The encapsulation unit encloses in the inner space (Vi) a main source of light emission of a given wavelength range comprised between 380 nm and 5 µm, preferably between 600 nm and 2200 nm, and/or an implanted sensing photodetector, either or both facing a wall portion forming a window having transmittance to the wavelength range. The main source of light emission is configured for sending pulses of light energy according to defined parameters, and wherein the implanted sensing photodetector is configured for receiving optical signals.

The tissue interaction unit is separate from the encapsulation unit and is configured for interacting with a tissue. The energy transfer lead comprises lead no electric conductive wire and comprises an optical fibre having, a proximal end coupled to the encapsulation unit and facing the window of the encapsulation unit in alignment with the main source of light emission and/or with the implanted sensing photodetector, and a distal end coupled to the tissue interaction unit.

In this embodiment, the electronic circuit is configured for controlling the implanted source of communication light, the implanted communication photodetector, the main source of light emission, and the implanted sensing photodetector. This embodiment is particularly suitable for neurostimulators, wherein an implanted pulse generator (IPG) is enclosed in the inner space (Vi) and comprises the main source of light emission, for sending pulses of light energy according to defined parameters. The electronic circuit is configured for controlling the IPG. The tissue interaction unit is either, an electrode unit comprising a photovoltaic cell coupled to one or more contact units, each including two, preferably three contacts, separated from one another and supported on a non-conductive support, wherein the distal end of the optical fibre is coupled to the electrode unit and faces the photovoltaic cell, or an optrode unit.

For example, the AIMD can be configured for stimulating a vagus nerve. The electrode unit forming the tissue interaction unit is suitable for coupling to a vagus nerve of the patient. The user interface of the external processing unit is configured for entering control pulse parameters of a control energy pulse and the external communication unit is in communication with the external processing unit and is configured for sending a signal to the electronic circuit instructing the implanted pulse generator (IPG) to emit signals representative of the control pulse parameters entered in the external processing unit, and received by the implanted communication photodetector.

In this embodiment, the kit-of-parts further comprises an external laryngeal controller comprising, a laryngeal electrode unit comprising laryngeal electrodes suitable for being coupled to a skin of a neck of the patient at the level of a laryngeal region and suitable for measuring a laryngeal electrical activity at the laryngeal region, and an external energy transfer lead comprising one or more optical fibres for transferring an optical signal from the laryngeal electrode unit to the external processing unit, the optical signal being representative of a laryngeal electrical activity measured by the laryngeal electrodes at the laryngeal region.

The external processing unit is configured for converting optical signals transferred by the external energy transfer lead into a visual, numerical, or acoustic form indicative of the intensity of the optical signal. This gives precious information that the pulses have been delivered as commanded, and the intensity of the signal gives a relative information on the intensity of the stimulation thus obtained.

In the same or in an alternative embodiment, the AIMD is (also) a monitoring device configured for monitoring biomarkers of the patient. The AIMD comprises one or more sensors located in the inner space (Vi) or in the tissue interaction unit if the kit-of-parts comprises one such tissue interaction unit. The one or more sensors comprise one or more optical sensors, and/or one or more of electroencephalogram (EEG), electrical muscular and neural activity sensor, accelerometer, hemodynamic activity sensor. The encapsulation unit preferably comprises no feedthrough for ensuring electric conductive communication across the walls of the encapsulation unit.

The present invention also concerns a system for visualizing by a magnetic resonance imaging (MRI) technique including a functional magnetic resonance imaging (fMRI) technique, regions of a central nervous system of a patient having an implanted active implantable medical device (AIMD). The system comprises, a kit-of-parts as discussed supra, a magnetic resonance (MR) device located in a Faraday cage, a control room (210) located outside of the Faraday cage, an MR controller for controlling the functions of the MR-device, a cage feedthrough, The AIMD of the kit-of-parts is implanted in the patient with the implanted source of communication light and the implanted communication photodetector facing towards an area of skin of the patient. The MR-device is configured for generating magnetic resonance images (MRI) or spectra (MRS), including functional magnetic resonance images (fMRI) or spectra (fMRS) of a central nervous system of the patient. The external processing unit, the external communication unit, which is in wireless communication or in wire or optical communication with the external processing unit, and the MR controller are all located in the control room.

The cage feedthrough is configured for providing a continuous optical communication via each of the one or more optical fibres of the optical communication lead between,
- a proximal end coupled to the external communication unit and located in the control room, and
- a distal end located in the Faraday cage, and coupled to the area of skin of the patient, in good alignment with the implanted source of communication light and/or the implanted communication photodetector of the encapsulation unit.

The external processing unit is thus in two-way communication with the electronic circuit of the encapsulation unit for transferring parameters and commands to the electronic circuit, and for displaying information sent from the implanted source of communication light.

In a preferred embodiment, the kit-of-parts comprises the three main components discussed supra. The external processing unit is in communication with the MR controller for synchronizing time sequences of MR images generation and of activations of one or more of the implanted source of communication light, the implanted communication photodetector, the main source of light emission, and the implanted sensing photodetector. If the AIMD is a vagus nerve stimulator and the kit-of-parts comprises an external laryngeal controller as discussed supra, the synchronizing time sequences of MR images generation and of activations of one or more of the implanted source of communication light includes taking as starting point in time for the synchronization the time when the external communication unit sends a signal to the electronic circuit of the encapsulation unit to instruct the implanted pulse generator (IPG) to emit signals representative of the control pulse parameters.

The present invention also concerns an active implantable medical device (AIMD) for implantation in a body of a patient and particularly suitable for use in the kit-of-parts and system discussed supra. The AIMD of the present invention comprises three main components discussed supra, viz.,
- an encapsulation unit,
- a tissue interaction unit separate from the encapsulation unit, and configured for interacting with a tissue, and
- an energy transfer lead.

As discussed supra, the encapsulation unit defines the inner space (Vi) sealingly separated from the outer environment by walls defined by the inner surface defining the boundaries of the inner space. The walls of the encapsulation are made of a ceramic material, preferably fused silica or a spinnel. The inner space contains:
- the implanted source of communication light and the implanted communication photodetector, each facing a portion of wall having a transmittance to wavelength of 500 to 1200 nm for optical communication with an exterior of the body,
- the main source of light emission of a given wavelength range comprised between 380 and 2200 nm and/or the implanted sensing photodetector, each facing a window having transmittance to the wavelength range; the main source of light emission is configured for sending pulses of light energy according to defined parameters, and the implanted sensing photodetector is configured for receiving optical signals,
- the electronic circuit for controlling the implanted source of communication light, the implanted communication photodetector, the main source of light emission, and the implanted sensing photodetector.

The energy transfer lead comprises no electric conductive wire and comprises an optical fibre having a proximal end coupled to the encapsulation unit and facing the window of the encapsulation unit in alignment with the main source of light emission and/or with the implanted sensing photodetector, and a distal end coupled to the tissue interaction unit.

The AIMD of the present invention yields a specific absorption rate (SAR) normalized to a background level of a phantom of not more than 4.0 dB, preferably nor more than 3.5 dB, more preferably not more than 3.2 dB, upon exposure to the following conditions. The AIMD is immersed in a saline composition of a phantom, which is composed of a tissue simulating medium having an electrical conductivity of 0.47 S/m and a relative permittivity of 78. The saline composition is maintained at a constant temperature. The phantom is placed inside a birdcage resonator compatible with ISO/TS 10974:2018 configured for exposing the implant fully immersed in the phantom at a depth of 65 mm to a magnetic field (B) oscillating at a frequency of f=64 MHz and inducing a constant tangential field (E) of 36.31 V_rms/m. The SAR is measured with sensors (4s-6s) positioned at 2 mm of the AIMD for 5 measuring the SAR of the encapsulation unit, of the energy transfer lead, and of the tissue interaction unit. The specific absorption rate (SAR) is the highest of the values measured at the three main components.

The AIMD of the present invention is preferably a neurostimulator wherein,
(a) the inner space contains an implanted pulse generator (IPG) comprising the main source of light emission for sending pulses of light energy according to defined parameters through the energy transfer lead to the tissue interaction unit and
(b) the tissue interaction unit forms,
   an electrode unit comprising a photovoltaic cell coupled to two, preferably three contacts, separated from one another and supported on a non-conductive support, or
   an optrode unit.

The neurostimulator is preferably fully functional in an MR-device in operation. The full functionality of an AIMD implanted in a patient can be determined as follows.
providing an external laryngeal controller comprising,
   a laryngeal electrode unit comprising laryngeal electrodes coupled to a skin of a neck of the patient at the level of a laryngeal region and suitable for measuring a laryngeal electrical activity at the laryngeal region, and
   an external energy transfer lead comprising one or more optical fibres for transferring an optical signal from the laryngeal electrode unit to the external processing unit, the optical signal being representative of a laryngeal electrical activity measured by the laryngeal electrodes at the laryngeal region,
positioning the patient in the MR-device wherein the AIMD is implanted with the electrode unit coupled to a vagus nerve, entering control pulse parameters of a control energy pulse into the external processing unit and instructing the implanted pulse generator (IPG) to emit signals representative of the control pulse parameters, measuring the laryngeal electrical activity at the laryngeal region with the laryngeal electrode unit with the MR-device at rest and with the MR-device activated in conditions suitable for generating MR-images (MRI) or functional MR-images (fMRI), comparing peaks of the laryngeal electrical activity representative of a propagation of the control pulses along the vagus nerve thus measured with the MR-device activated with the ones measured with the MR-device at rest, The AIMD is fully functional in an MR-device in operation if a height and a full width at half maximum (FWHM) of the peaks measured with the activated MR-device do not deviate by more than ±10%, preferably not more than ±5% of the ones of the peaks measured with the MR-device at rest.

The full functionality of an AIMD which is not implanted in a patient can be determined as follows by applying MR tests using the testing criteria provided in § 17 of ISO TS 10974:2018, functional states of the AIMD are checked before, (if possible) during, and after the test, with the electronic circuit of the AIMD being configured to perform a cycling test defined by the following parameters:
standard stimulation at 1000 µA, 30 Hz, 7 s ON time, 128 bytes-memory data transfer from a defined RAM zone to another,
memory write of 128 incremental bytes to RAM,
stop stimulation for 12 s, real-time monitoring of the AIMD output is recorded and displayed on an oscilloscope, preferably located outside of the Faraday cage, the oscilloscope being in optical communication through an optical fibre,
with a light source connected to the contacts of the electrode unit, or
with the optrode unit, emitting optical signals representative of the pulses of light energy sent by the main source of light emission of the IPG, The AIMD is considered as fully functional if the following conditions are fulfilled:
the variation of the outputs before, during, and after the MR test are within the following ranges,
the variation of a frequency of the pulses of light energy is not more than ±5%, preferably not more than ±1%, and
the variation of a pulse duration is not more than ±5%, preferably not more than ±1%, and
the variation of an amplitude is not more than ±10%, preferably not more than ±5%, more preferably not more than ±1%, and
a duty cycle (=time ON/(time ON+time OFF)) is comprised between 36 and 38% before, during, and after the MR test, and
no corruption of the RAM and, preferably no corruption of the ROM and/or no unexpected system reset, is identified before, and after the MR test.

BRIEF DESCRIPTION OF THE FIGURES

For a fuller understanding of the nature of the present invention, reference is made to the following detailed description taken in conjunction with the accompanying drawings in which:

FIG. 4: shows examples of tissue interaction units (a) and (b) electrode units with a pulse control light coupled to an oscilloscope and to the implanted photodetector, respectively, and (c) optrode with pulse control light coupled to an oscilloscope.

FIG. 6: Shows a system according to the present invention, (a) general view, (b) detail of the proximal interface device between proximal end of the optical fibre and external communication unit and (c) detail of the distal interface device, between the distal end of the optical fibre and the skin of the patient.

DETAILED DESCRIPTION OF THE INVENTION

Figure 1:
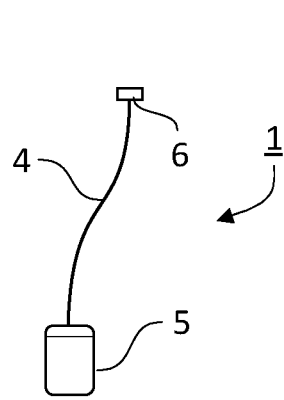
FIG. 1: shows an AIMD according to the present invention.

A kit-of-parts according to the present invention is suitable for visualizing by a magnetic resonance imaging (MRI) technique including a functional magnetic resonance imaging (fMRI) technique, regions of a central nervous system of a patient (51) having an implanted active implantable medical device (AIMD) (1). The central nervous system includes the brain and spinal cord. As illustrated in FIG. 6(a), the kit-of-parts comprises,
the AIMD (1),
an external processing unit (100),
an external communication unit (102) in communication with the external processing unit (100),
an optical communication lead (104) comprising an optical fibre (1040 for establishing an optical communication between the AIMD and the external communication unit (102).

The external processing unit (100) forms an interface between the kit-of-parts and an operator and allows control of the various components of the kit-of-parts. Instructions entered by the operator via a user interface into the external processing unit (100) can be transmitted by wireless, optical or wired communication to the external communication unit (102). The external communication unit (102) transfers the instructions by emission of optical signals through the optical fibre (1040 of the optical communication lead (104)

to the implanted AIMD (1). The optical signals are transmitted from the optical fibre (1040 to the implanted AIMD through the skin (50) of the patient (51) implanted with the AIMD. No electrically conductive wire is used between the external communication unit (102) and the AIMD implanted in the body of the patient. This is important for safety and reliability reasons when the patient is exposed to magnetic image acquisition conditions in an MR-device (200).

Magnetic resonance imaging (MRI), including functional magnetic resonance imaging (fMRI) is a powerful tool for visualizing internal organs of a patient and for tracking the activity thereof. As discussed in the section "Background of the Invention", however, patients wearing an implanted AIMD must be prudent as the various electromagnetic fields involved in an image acquisition sequence can interact with the components of the AIMD, possibly leading to the degradation of the AIMD or to serious tissue injuries, typically by burning. The basic principles of MRI are described in continuation, followed by the description of the AIMD and other components of the invention for taking advantage of the potential of MRI to a further development of neurostimulation.

Magnetic Resonance Imaging Device (200)

A magnetic resonance imaging device (200) (MR-device) implements a medical imaging technique based on the interactions of excitable atoms present in an organic tissue of the patient (51) with electromagnetic fields. When placed in a strong main magnetic field (B0) the spins of the nuclei of said excitable atoms process around an axis aligned with the main magnetic field (B0), resulting in a net polarization at rest that is parallel to the main magnetic field (B0). The application of a pulse of radio frequency (RF) exciting magnetic field (B1), at the frequency of resonance (fL), called the Larmor frequency, of the excitable atoms in said main magnetic field (B0) excites said atoms by tipping the net polarization vector sideways (e.g., with a so-called 90° pulse, B1 90) or to angles greater than 90° and even reverse it at 180° (with a so-called 180° pulse, B1 180). When the RF electromagnetic pulse is turned off, the spins of the nuclei of the excitable atoms return progressively to an equilibrium state yielding the net polarization at rest. During relaxation, the transverse vector component of the spins produces an oscillating magnetic field inducing a signal which can be collected by antennas (200a) located in close proximity to the anatomy under examination.

Figure 5A:
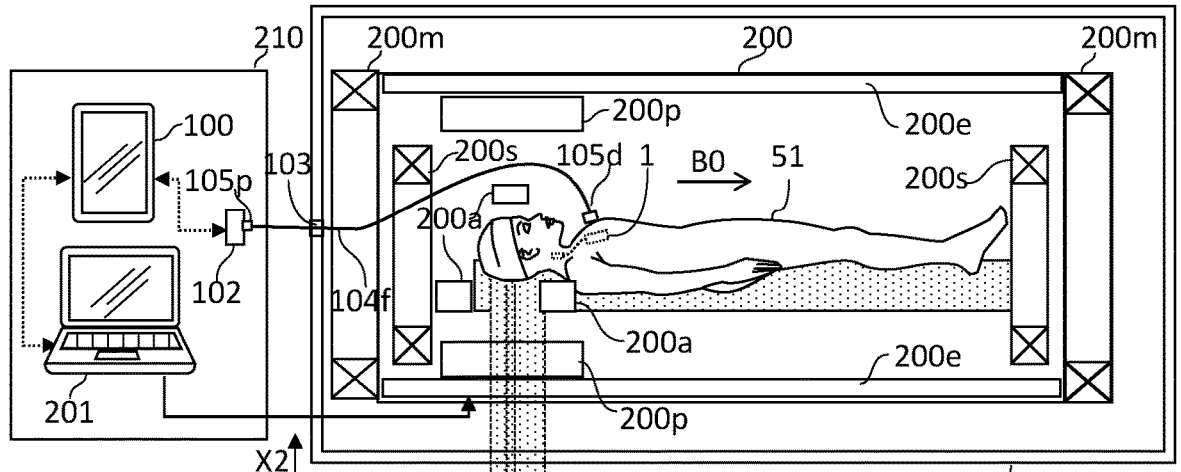
FIG. 5: shows an MR-device (a) and (d) side view and front view, (b) and (c) gradients of the magnetic field and Larmor resonance frequency as a function of the position along an axis x1.
Figure 5B:
Figure 5C:
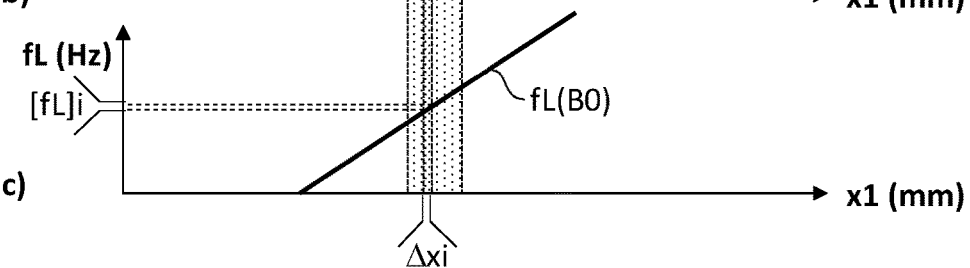
Figure 5D:
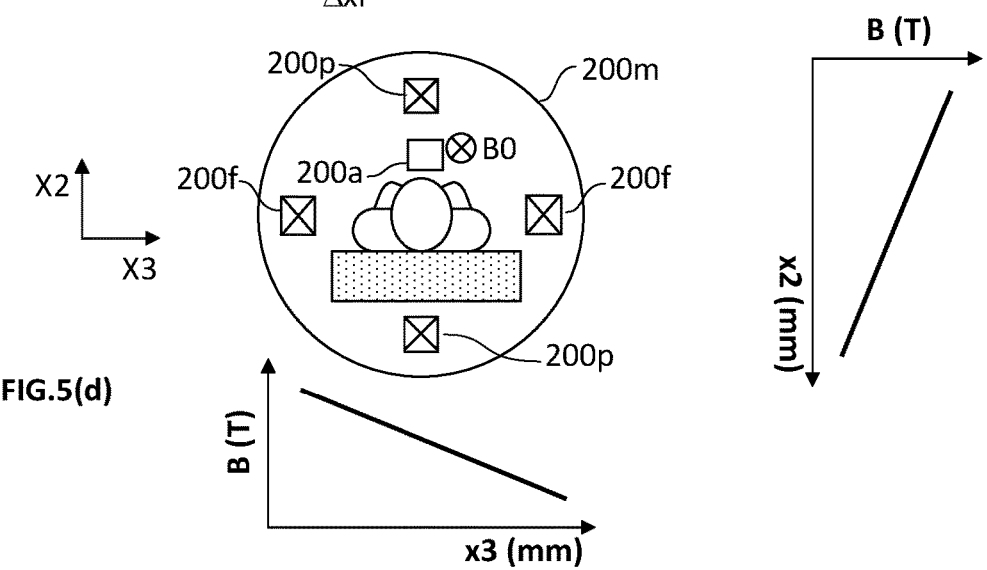

As shown in FIGS. 5(a) to 5(d), a MR-device (200) usually comprises,
- a main magnet unit (200m) for creating a uniform main magnetic field (B0);
- radiofrequency (RF) excitation coils (200e) for creating the RF exciting magnetic field (B1),
- X1, X2, and X3 gradient coils (200s, 200p, 200O for creating magnetic gradients along the first, second, and third directions X1, X2, and X3, respectively, as shown in FIG. 5(c) for a gradient along X1, and FIG. 5(d) for gradients along X2 and X3, and
- antennas (200a), for receiving RF-signals emitted by excited atoms as they relax from their excited state back to their rest state.

The main magnet unit (200m) produces the main magnetic field (B0) and can be a permanent magnet or an electro-magnet (a supra-conductive magnet or not). An example of a suitable MR-device includes, but is not limited to, a device described in U.S. Pat. No. 4,694,836.

In one embodiment, magnetic resonance images of a volume, Vp, inside the body of the patient can be created by capturing images slice by slice, one slice having a volume, Vpi, of thickness, Δxi, normal to the first direction, X1. As shown in FIG. 5(c), because the Larmor frequency (fL) of an excitable atom depends on the magnitude of the magnetic field it is exposed to, sending pulses of RF exciting magnetic field (B1) at a frequency range, [fL]i, excites exclusively the excitable atoms which are exposed to a magnetic field range, [B0]i. By creating a magnetic field gradient along the first direction, X1, only the atoms located in a slice or layer, Vpi, of thickness, Δxi, exposed to a magnetic field range, [B0]i are excited by the frequency range, [fL]I, as shown in FIG. 5(b).

To localize the spatial origin of the signals received by the antennas (200a) on a plane normal to the first direction, X1, magnetic gradients are created successively along second and third directions, X2, X3, wherein X1⊥X2⊥X3, by activating the X2 and X3 gradient coils (200p, 200f), as illustrated in FIG. 5(d). Said gradients provoke a phase gradient, Δφ, and a frequency gradient, Δf, in the spins of the excited nuclei as they relax, which allows spatial encoding of the received signals in the second and third directions, X2, X3. A two-dimensional matrix is thus acquired, producing k-space data, and an MR image is created by performing a two-dimensional inverse Fourier transform. Other modes of acquiring and creating an MR-image are known in the art and the present invention is not restricted to the selection of any particular mode. It suffices to understand that electromagnetic fields of high magnitude and/or high frequencies are required for acquiring an MR-image.

The main magnetic field, B0, is generally comprised between 0.2 and 7 T, preferably between 1 and 4 T. The radiofrequency (RF) excitation coils (200e) generate a magnetic field at a frequency range [fL]i around the Larmor frequencies (fL) of the atoms comprised within a slice of thickness, Δxi, and exposed to a main magnetic field range [B0]i. For atoms of hydrogen, the Larmor frequency per magnetic strength unit, $fL/B=42.6$ MHz $T^{-1}$. For example, for hydrogen atoms exposed to a main magnetic field, B0=1.5 T, the Larmor frequency, fL≈64 MHz, and for a main magnetic field, B0=3 T, the Larmor frequency, fL≈128 MHz. For a main magnetic field, B0=7 T, the Larmor frequency, fL≈298 MHz.

The MR-device (200) can be any of a closed-bore, open-bore, or wide-bore MR-device type. A typical closed-bore MR-device has a magnetic strength of 1.0 T through 3.0 T with a bore diameter of the order of 60 cm. An open-bore MR-device has typically two main magnet poles (200m) separated by a gap between them for accommodating a patient in a lying position, sitting position, or any other position suitable for imaging an imaging volume, Vp. The magnetic field of an open-bore MR-device is usually comprised between 0.2 and 1.0 T. A wide-bore MR-device is a kind of closed-bore MR-device having a larger diameter.

Functional magnetic resonance imaging (fMRI) measures brain activity by monitoring blood flow. Assuming that cerebral blood flow and neuronal activation are coupled implies that when an area of the brain is in use, additional blood flows to that region. Blood-oxygen-level dependent (BOLD) contrast allows mapping neural activity in the brain or spinal cord of a patient by imaging the changes in blood flow (hemodynamic response) related to energy use by brain cells. The resulting brain activation can be characterized by a spectrum or represented graphically by colour-coding the strength of activation across the brain or the specific region studied. The location accuracy of detection can be of the order of the millimetre. Other fMRI methods include arterial spin labelling and diffusion MRI, which is similar to BOLD fMRI but provides contrast based on the magnitude of diffusion of water molecules in the brain.

Combining fMRI monitoring with stimulation of a tissue, such as the vagus nerve, or others, with varying stimuli parameters, can substantially enhance the understanding of the mechanisms underlying the promising results observed with neurostimulation in the treatment of diseases like epilepsy, Parkinson, and the like. Furthermore, rather than each medical practitioner using one (or only a limited number of) set(s) of parameters which fits all the patients as is basically the case now, with some tuning based on the patient feedback, the system of the present invention permits to optimize "a la carte" a set of pulse parameters optimized for each individual patient, based on solid, scientific data obtained by fMRI.

The kit-of-parts of the present invention is among the best suited for use with a state of the art MR-device (200), in a system according to the present invention.

AIMD (1)—Simplest Form

An AIMD (1) implanted in a patient (51) must be harmless when the patient is positioned in an MR-device (200) during an MR-image acquisition session. In its simplest form, the AIMD comprises an encapsulation unit (5) comprising a housing defining an inner space (Vi) sealingly separated from an outer environment by walls. The walls are defined by an inner surface defining the boundaries of the inner space. Because the magnitude of the current induced by exposure to a varying magnetic field is proportional to conductivity, significant current densities may be generated in metals used in implants. For this reason, the housing of the encapsulation unit (5) is made of a non-metallic and non-conductive material. A non-conductive material is defined as a material having a conductivity lower than $10^3$ S/m. It is also preferred that the AIMD be made substantially only of materials having a magnetic susceptibility, $|\chi|<2 \cdot 10^{-2}$, preferably $|\chi|<10^{-2}$, wherein the magnetic susceptibility is expressed relative to volume and is dimensionless [$m^3/m^3$], as materials having a magnetic susceptibility, $|\chi|>2 \cdot 10^{-2}$, experience strong magnetic forces and torques and create image distortion and degradation even at locations remote from the imaging region.

For example, it is preferred that the non-metallic material of the housing be selected among ceramic and polymers, preferably a ceramic, more preferably fused silica or a spinel.

Figure 2:
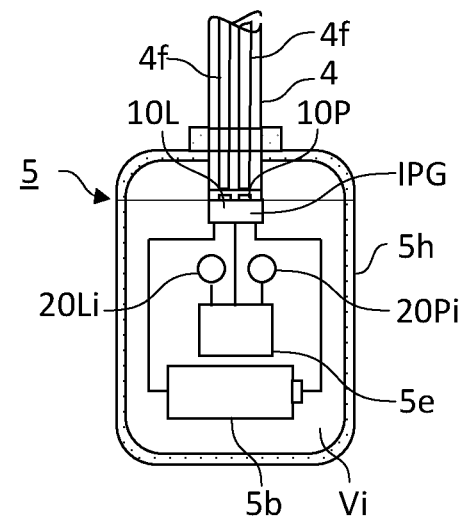
FIG. 2: shows an encapsulation unit of an AIMD according to FIG. 1, with contents of the inner space thereof.

As shown in FIG. 2, the inner space of the encapsulation unit contains:
- an implanted source of communication light (20Li) and an implanted communication photodetector (20Pi) for optical communication with the outer environment of the body and
- an electronic circuit (5e) for controlling the implanted source of communication light (20Li) and the implanted communication photodetector (20Pi), for the communication with an exterior and, optionally, for monitoring biomarkers.

Each of the implanted source of communication light (20Li) and implanted communication photodetector (20Pi) faces a portion of wall having a given transmittance to a wavelength range. The given transmittance is preferably of at least 70%, more preferably at least 80%, most preferably at least 90%, averaged over a range of ±20 nm around the wavelength actually used, or over the mean value of a wavelength range actually used.

The source of communication light can be used for sending information from the AIMD to an external unit (100, 102) located outside the body of the patient. Similarly, the implanted communication photodetector (20Pi) can be used for receiving information or instructions from the external unit (100, 102). The wavelength used for such communication is generally selected within the range comprised between 500 and 1200 nm. The portion(s) of wall faced by both source of communication light (20Li) and implanted communication photodetector (20Pi) must have the given transmittance to selected values comprised at least within said range of wavelengths comprised between 500 and 1200 nm.

The source of communication light (20Li) and implanted communication photodetector (20Pi) can also be used for monitoring biomarkers, e.g., volumetric blood changes induced by cardiac pulsations or arterial oxygen saturation values ($SpO_2$) by photoplethysmography (PPG). The source of communication light (20Li) emits a radiation of given wavelength, and the implanted communication photodetector (20Pi) records the light diffracted or reflected by the tissues thus irradiated. The radiations used for performing such monitoring can have wavelengths selected within the range comprised between 380 nm and 5 µm, preferably between 600 nm and 2200 nm. For purposes of biomarkers monitoring, the portion(s) of wall faced by both source of communication light (20Li) and implanted communication photodetector (20Pi) must have the given transmittance to selected values comprised within said range of wavelengths comprised between 380 nm and 5 µm, preferably between 600 nm and 2200 nm. It is clear that a different set of source of light and of implanted photodetector from the set of source of communication light (20Li) and of implanted communication photodetector (20Pi) can be used for monitoring biomarkers, as the orientation of the latter set may not be optimal for carrying out such monitoring for specific tissues.

In a preferred embodiment, wherein the housing is made of a ceramic material, such as fused silica or a spinel, the portion of wall preferably has a transmittance to a wavelength of 850 nm at room temperature of at least 75%.

The electronic circuit (5e) controls at least the communication with the exterior of the encapsulation unit through the source of communication light (20Li) and the implanted communication photodetector (20Pi). As such, the electronic circuit ensures that the source of communication light (20Li) is activated to communicate data or other information by radiation through the portion of wall. Additionally, the electronic circuit (5e) must be able to implement instructions optically received from the exterior through the portion of wall by the implanted communication photodetector (20Pi).

In case the set of source of communication light (20Li) and implanted communication photodetector (20Pi) (or another set) are used for monitoring biomarkers, the electronic circuit (5e) should also be capable of first, controlling the activation of the source of communication light (20Li) to emit a radiation of selected wavelength and, second, instructing the source of communication light (20Li) to transmit data representative of the results measured by the implanted communication photodetector (20Pi) to the exterior.

Three-Part AIMD (1)

In a preferred embodiment illustrated in FIG. 1, the AIMD is formed by three parts:
- the encapsulation unit (5) discussed supra and configured for being subcutaneously implanted in the patient body at a location remote from the tissue to be interacted with, an energy transfer lead (4) comprising an optical fibre (40 and ensuring optical communication from/to the encapsulation unit (5) to/from a tissue interaction unit (6) configured for interacting with a tissue remote from the implantation location of the encapsulation unit (5).

The encapsulation unit (5) is as discussed supra and further encloses in the inner space (Vi), a main source of light emission (10L) of a given wavelength range comprised between 380 nm and 5 µm, preferably between 600 nm and 2200 nm, and/or an implanted sensing photodetector (10P).

The main source of light emission (10L) and/or implanted sensing photodetector (10P) face a wall portion forming a window having transmittance to the wavelength range, wherein the main source of light emission (10L) is configured for sending pulses of light energy according to defined parameters, and wherein the implanted sensing photodetector (10P) is configured for receiving optical signals.

The electronic circuit (5e) is configured for controlling the implanted source of communication light (20Li), the implanted communication photodetector (20Pi), the main source of light emission (10L), and/or the implanted sensing photodetector (10P). For example, the electronic circuit (5e) can be configured for instructing the main source of light emission (10L) to emit light pulses according to parameters received from the exterior by the implanted communication photodetector (20Pi).

Alternatively, or concomitantly, the electronic circuit (5e) can be configured for instructing the implanted source of communication light (20Li) to emit light signals to the exterior representative of data received by the implanted communication photodetector (20Pi) or by the implanted sensing photodetector (10P).

The energy transfer lead (4) comprises at least one optical fibre (40 and comprises no electric conductive wire. The optical fibre (40 has a proximal end coupled to the encapsulation unit (5) and facing the window of the encapsulation unit in alignment with the main source of light emission (10L) and/or with the implanted sensing photodetector (10P). The optical fibre has a distal end coupled to the tissue interaction unit discussed below. This ensures optical communication from/to the main source of light emission (10L) and/or with the implanted sensing photodetector (10P) to/from the tissue interaction unit (6).

The tissue interaction unit (6) is separate from the encapsulation unit and optically coupled to the latter by the energy transfer lead (4). The tissue interaction unit (6) is configured for interacting with a tissue remote from the implantation location of the encapsulation unit (5). The tissue interaction unit (6) can be an electrode unit (6e) as illustrated in FIGS. 3(a) to 3(c), 4(a) and 4(b), and 6, or an optrode unit (60) as shown in FIG. 4(c). An electrode unit (6e) delivers or measures electrical signals to or from the treated tissue, whereas an optrode unit (60) emits or receives optical signals towards or from the treated tissue.

The tissue interaction unit (6) comprises an insulating support for supporting the contacts (7+, 7−) of an electrode unit (6e) or for supporting the optical components of an optrode unit (60), including the distal end of the optical fibre (40, and any micro-optical components (4L) such as lenses, e.g., Fresnel lenses, collimators, diffusors, and the like. The geometry of the support depends on the tissue to be treated. For example, if the tissue has a cylindrical geometry, such as a nerve (e.g., a vagus nerve), the support can form a cuff configured for wrapping around the nerve, as illustrated in FIGS. 3(a) and 3(b), 4(a) to 4(c), 6(a), 8, and 9 (cf. e.g., EP3471820B1 and EP3512597B1). For insertion into a brain, the support forms an elongated cylinder as shown in the deep brain electrode illustrated in FIG. 3(c). Other geometries of electrode and optrode units for interacting with other tissues are well known in the art, and the choice of a specific geometry does not affect the present invention.

The insulating support of a cuff electrode unit (6e) comprises a nerve coupling surface, which 5 may contact the nerve to be treated without causing any neural stimulating effect. The insulating support is used for securing the contacts (or electrodes) at their treatment positions for long term implantation, and for reducing stray currents. The insulating support is preferably made of a polymeric material. If the insulating material must be deformed for insertion and for accommodating any body movement, such as with a self-sizing cuff electrode illustrated in FIG. 3(a), it is preferably made of an elastomeric polymer, such as silicone or a polyurethane elastomer, or can be made of a sheet of polyimide. For other electrode geometries, such as slit cuff electrodes, the insulating support can be rigid and made for example of polyurethane or of an epoxy resin. The resistance of the tissue is of the order of 3-5 kΩ. With a current of the order of 0.1 to 3 mA, the voltage required between contacts (7+, 7−) can be of the order of 10 V.

As illustrated in FIG. 4(c), instead of, or additionally to electrode contacts (7+, 7−), the insulating support sheet can be provided with one or more optical contacts to form an optrode unit (60). An optical contact as defined herein can be either a light emitter or a light sensor, or both. In some applications, stimulation of a tissue by light emission is mainly due to localized heating of the tissue. For such applications, it is preferred that the light directed by the optical contact be in the infrared range, preferably in the range of 750 to 3000 nm, more preferably of 1200 to 1800 nm. The cuff optrode suitable for the present invention, however, can be used with light beams of any wavelength compatible with the main source of light emission (10L).

An optical contact or optrode can be the end of an optical fibre, which is either bevelled or coupled to a lens, mirror, or other micro-optic device for directing and focusing a light beam towards a precise area of the tissue to be treated. The optrode can be optically coupled to an optical fibre (40 of an optical energy transfer lead (4), and to an optical IPG housed in the encapsulation unit (5).

The tissue interaction unit (6) can be used for stimulating a tissue (e.g., vagus nerve stimulation (VNS)), or for monitoring a biomarker at a location remote from the implantation location of the encapsulation unit (5).

Three-Part AIMD (1)—Tissue Stimulator

In a preferred embodiment of the present invention, the AIMD is a neurostimulator configured for stimulating a tissue coupled to the tissue interaction unit. As illustrated in FIGS. 2 and 4(a) to 4(c) in this embodiment, the encapsulation unit (5) encloses in the inner volume (Vi) an implanted pulse generator (IPG) comprising or coupled to the main source of light emission (10L), for sending pulses of light energy according to defined parameters. The pulses of light energy propagate through the window, along the optical fibre (40 to the tissue interaction unit (6). The defined parameters are received by the electronic circuit (5e) from an external unit through the implanted communication photodetector (20Pi). The electronic circuit (5e) is configured for controlling the IPG according to the defined parameters.

FIG. 4(a) illustrates an embodiment of a cuff electrode unit (6e). The electrode unit (6e) comprises a photovoltaic cell (6v) coupled to one or more contact units, each including two, preferably three contacts (7+, 7−), separated from one another and supported on the insulating support. The photovoltaic cell is in optical communication with the distal end of the optical fibre (40 of the energy transfer lead (4) coupled to the electrode unit (6e). The photovoltaic cell (6v) is coupled to the contacts (7+, 7−) by nerve-connection wires (cf. FIG. 3(b)) for transforming optical energy into electrical energy, which is conducted to the contacts (7+, 7−) by the nerve-connection wires. To reduce heating when exposed to varying electromagnetic fields, it is preferred that the nerve-connection wires be as short as possible and preferably not more than 50 mm long, preferably not more than 30 mm long, more preferably not more than 20 mm long, most preferably not more than 15 mm long. It is generally accepted that conductive wires of not more than 20 mm yield no substantial heating effect when exposed to MR-image acquisition conditions, as reported in ASTM F21 82-1 9e2, page 1, § 1.7, which states that "a device with deployed dimensions of less than 2 cm in all directions does not need to be tested with respect to RF-induced heating, as it is expected to generate Delta T of less than 2° C. over 1 hour of exposure at 1.5 T and 3 T frequencies."

The energy pulses of optical energy propagating along the optical fibre (40 reach the photovoltaic cell (6v) which transforms the optical energy into electrical energy, which is conducted to the two or more contacts (7+, 7−) of each of the one or more contact units.

FIG. 4(c) illustrates an example of optrode (60) comprising an insulating support holding the distal end of an optical fibre (40 of the energy transfer lead (4), such as to point the pulses of optical 5 radiations towards a desired area of the tissue to be treated. The distal end of the optical fibre (40 can be cut in a desired way, e.g., with a bevelled edge, and/or be provided with micro-optical elements (4L) located between the distal end of the optical fibre (40 and a surface of the tissue to be stimulated.

Micro-optical elements (4L) such as lenses (e.g., Fresnel lenses), collimators, mirrors, and the like, can be provided between the proximal end of the one or more optical fibres (40 and the main source of light emission (10L) and/or the implanted sensing photodetector (10P), to optimize the shape of the light beams. For example, they can be positioned on a surface of the window, or on the proximal end of the optical fibres (40.

An example of encapsulation unit suitable for the present invention and comprising an optical IPG is described in EP3400057B1.

Vagus Nerve Neurostimulator and Laryngeal Control

A nerve typically consists of a bundle of nerve fibres. A nerve is activated by a stimulation pulse if at least one of its nerve fibres triggers an action potential, which propagates along its length. An action potential is triggered by a local depolarisation of the membrane of the nerve fibre. The membrane potential rapidly rises and falls causing adjacent locations to similarly depolarise. This depolarisation then propagates along the nerve fibre. When several nerve fibres are activated, the sum of all these action potentials that propagate within the nerve is called a compound action potential (CAP).

Figure 7A:
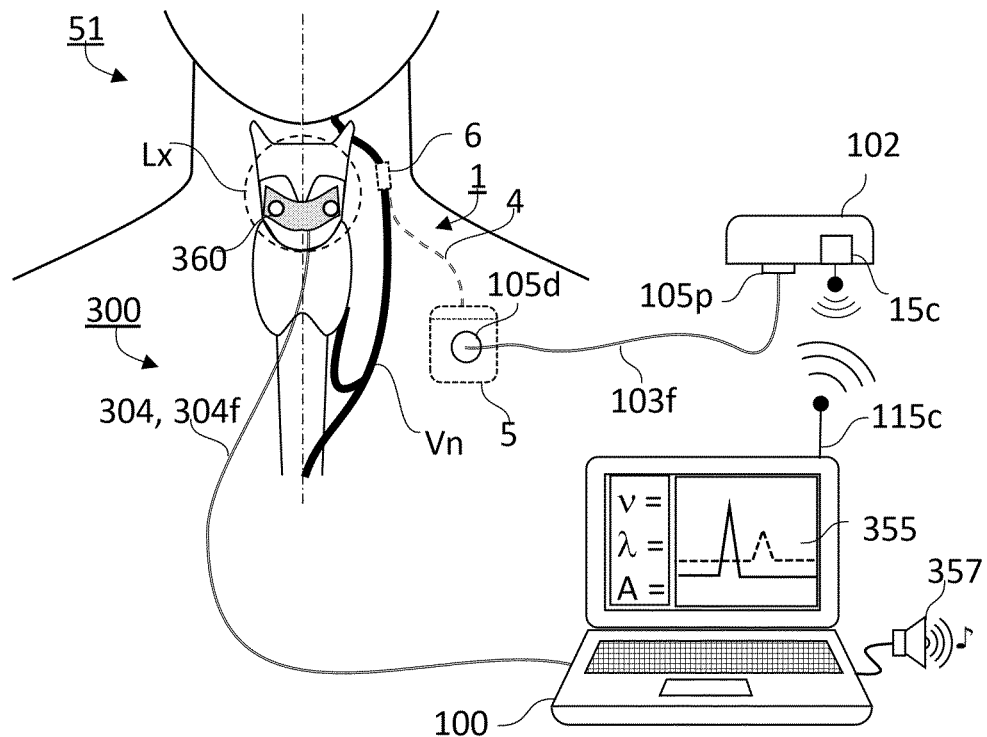
FIG. 7: Shows an example of (a) external laryngeal controller, and (b) of the laryngeal electric activity measured with the device of (a), identifying that an energy pulse was delivered to the vagus nerve and generated an electrical peak at the laryngeal zone.

In a preferred embodiment illustrated in FIG. 7(a), the electrode unit (6e) is suitable for coupling to a vagus nerve (Vn) of the patient (51) and comprises an external laryngeal controller (300) configured for controlling that an energy pulse has been delivered to the vagus nerve, and that a compound action potential (CAP) has propagated along the vagus nerve and along the branching laryngeal nerve. This is of course a very important check, as there is otherwise no guarantee that, electrical pulses according to the defined parameters have been delivered to the vagus nerve, depending on a defect of the AIMD, for example,
  in the communication of the parameters to the electronic circuit (5e) or to the IPG, or
  in a connection between the electronic circuit (5e), the IPG, and the main source of light emission, or
  in the optical fibre (40 or coupling thereof, or
  in the photovoltaic cell and or contacts (7+, 7−), and connections thereof, or that,
a CAP has been created in the vagus nerve, and that it has propagated along the vagus nerve fibres, depending on a defect,
  in the contact between the contacts (7+, 7−) and the vagus nerve (Vn), or
  on the vagus nerve itself, which may be damaged or injured.

As shown in FIG. 7(a), the external laryngeal controller (300) comprises a laryngeal electrode unit (360) comprising laryngeal electrodes (361) suitable for being coupled to a skin (50) of a neck of the patient (51) at the level of a laryngeal region (Lx) and suitable for measuring a laryngeal electrical activity at the laryngeal region. An external energy transfer lead (304) is provided, which comprises one or more optical fibres (3040 for transferring an optical signal from the laryngeal electrode unit to the external processing unit (100) discussed in continuation, either directly, or through an intermediate external controller in communication with the external processing unit (100). The optical signal is representative of a laryngeal electrical activity measured by the laryngeal electrodes (361) at the laryngeal region. The external processing unit (100) is configured for converting the optical signals transferred by the external energy transfer lead into a visual (355), numerical, or acoustic (357) form indicative of the intensity of the optical signal.

The laryngeal electrodes can be coupled to a light source (e.g., a LED) in optical contact with the optical fibre (3040 to transfer an optical signal to the external processing unit (100). In order to strengthen the signal, the laryngeal electrodes can be electrically coupled to a signal treating circuit including an amplifier, and filters can be used to remove part of the background noise. For example, the signal can be pre-amplified with a first amplifier providing high input impedance, yielding amplification of the laryngeal electrical signal while removing the common mode component, thus yielding an amplified signal with enhanced signal to noise ratio. The amplified signal can be filtered by a filter such as a high pass filter configured for removing any remaining DC component of this common mode, mainly due to unequal electrode contacts potentials. This can be followed by a second amplifier configured for providing further amplification. This can be followed by a low-pass filter. In some embodiments, it is preferred to transfer an analog laryngeal electrical signal, and the amplified and filtered laryngeal electrical signal can be used to modulate the current fed to the LED in direct optical contact with the optical fibre (3040. In another embodiment, the amplified and filtered signal can be modulated in frequency (AL, FM, etc.), by e.g., converting the tension of the amplified and filtered laryngeal-signal into modulation of frequency (−v to +v signal being transformed into a sine curve of frequency varying between f1 and f2). In other embodiments, the amplified and filtered laryngeal-signal can be digitized in an analog-to-digital (A/D) converter to yield a digitized laryngeal-signal to be transferred through the signal transfer lead (4) in the form of optical energy. The digitized laryngeal-signal can be modulated in frequency, baseband, and the like, as well known by a skilled person. A driver can also be included, for modulating as described supra, and/or driving the thus treated laryngeal-signal through the signal transfer lead (4). The driver can be configured for supplying enough current to activate the LED. The driver can also convert a 0/1 digitized laryngeal-signal into a corresponding tension signal, e.g., 0V/5 V, or a current signal, e.g., 0 mA/4 mA).

To stabilize the laryngeal electrodes (361) at the laryngeal region (Lx) and to ensure an optimal contact with the laryngeal region, the laryngeal electrodes are supported on the inner surface of a support sheet. The inner surface may be provided with an adhesive layer, extending along at least a portion of the perimeter of the support sheet, or extending over part or all of the area of the inner surface. The adhesive can be a pressure sensitive adhesive (PSA) or any adhesive used in medical adhesive tapes or plasters. Alternatively, or additionally, straps can be provided to fix the laryngeal electrodes (361) to the laryngeal region (Lx).

Rather than looking at an unknown position in time for a peak in the laryngeal electrical activity representative of a CAP having propagated along the vagus nerve (Vn) and along the laryngeal nerve, branched to the vagus nerve, and having reached the laryngeal region (Lx) amid a potentially noisy laryngeal electrical activity background, the external processing unit (100), which is in communication with both external laryngeal controller (300) and AIMD (1) (through the external communication unit (102) discussed in continuation), is configured for instructing the electronic circuit (5e) and IPG of the encapsulation unit to trigger a control pulse (355c) at a known time (tv). Since the expected propagation time of the CAP to the laryngeal region (Lx) is known, an operator knows at what time (tlx) to expect a peak (355L) representative of the control energy pulse. By repeating the triggering of the control pulse several times, the background noise of the laryngeal electrical activity can be substantially reduced, and filtered, and the resolution of the peak (355L) enhanced accordingly. To this end, the external processing unit (100) is configured for entering control pulse parameters of a control energy pulse (355c) through the user interface. Said control pulse parameters are transferred to the electronic circuit (5e) instructing the implanted pulse generator (IPG) to emit signals representative of the control pulse parameters entered in the external processing unit (100) and received by the implanted communication photodetector (20Pi).

Figure 3A:
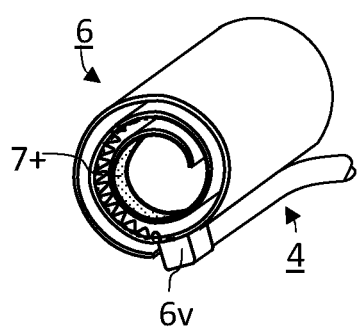
FIG. 3: shows electrode units, (a) and (b) cuff electrode units suitable for coupling to a nerve, e.g., the vagus nerve, and (c) deep brain electrodes.
Figure 3B:
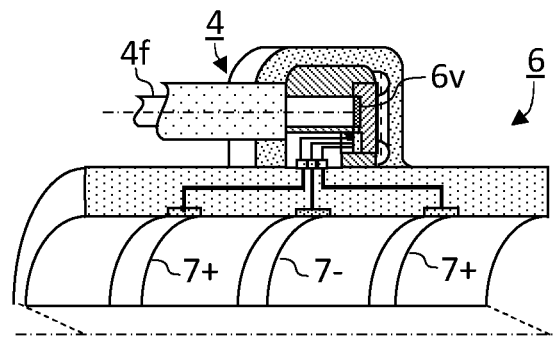
Figure 3C:
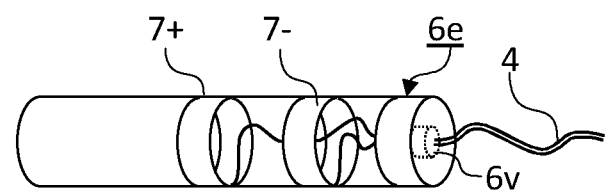
Figure 7B:
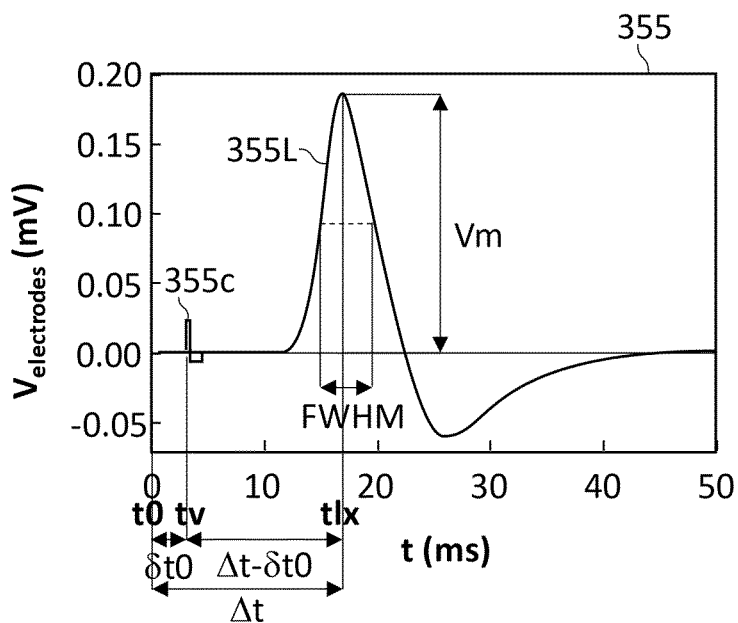

FIG. 7(b) illustrates an example of graphical representation (355) on the display of the external processing unit (100) of the electrical activity of the vagus nerve thus measured as a function of time. Through the external processing unit (100) the time (tv) at which a control pulse is emitted is known with great accuracy. Note that if the electrode unit is well designed and stray currents propagating outside the electrode unit are minimized, the control pulse (355c) represented in FIG. 7(b) is not visible, but it suffices that the position in time (tv) thereof be known. Stray currents propagating outside the electrode unit can be minimized for example by inter alia coupling three contacts (7+, 7−) to the photovoltaic cell, as illustrated in FIG. 3(b), so as to contain the current confined within the insulating support. After a period (Δt−δt0) following the triggering of the control pulse at time (tv), which can be estimated with considerable accuracy, a peak (355L) representative of the propagation of a CAP is expected. If no peak appears after approximately said period (Δt−δt0), a problem has arisen and the CAP has not propagated along the vagus nerve, branching into the laryngeal nerve to the laryngeal region (Lx). The origin of the problem must be investigated. If, as expected, a peak (355L) appears as illustrated in FIG. 7(b), the CAP resulting from the control pulse (355c) has reached the laryngeal region (Lx). The peak (355L) can be characterized by a height (Vm) and a full width at half maximum (FWHM) of the peak (355L). Comparison of these dimensions between measurements in different conditions yields a fair characterization of the stimulation actually applied to the vagus nerve An external laryngeal controller (300) suitable for the present invention is described in the European patent application EP18829318.

Monitoring AIMD (1)

Alternatively, or additionally to a stimulation function as discussed supra, the AIMD can fulfil a monitoring function. In order to monitor biomarkers of the patient (51) the AIMD comprises one or more sensors located in the inner space (Vi) or in the tissue interaction unit (6). The sensors can be optical sensors or non-optical sensors. The following non-exhaustive list are suitable non-optical sensors, including an accelerometer, glucose monitoring sensor, electroencephalogram (EEG), electrocardiogram (ECG), electrical muscular and neural activity sensor, hemodynamic activity sensor, pressure sensor, temperature sensor, or chemosensor. Some of the foregoing non-optical sensors are electric sensors measuring the electrical activity of a tissue by means of electrodes applied to the tissue at the exterior of the housing. In order to avoid using conductive wires coupled to feedthroughs for transferring an electric signal from the conductive wires to the inner space (Vi) of the encapsulation unit (5), electric sensors are located in the tissue interaction unit (6) in optical communication with the 5 encapsulation unit via the energy transfer lead (4) comprising an optical fibre as defined supra. For example, FIG. 4(b) illustrates an electrode unit (6e) comprising contacts (7+, 7−) applied to a tissue (52), such as a nerve. The contacts are electrically coupled to a light source (30L) in optical communication with the optical fibre (40 of the energy transfer lead (4) whose proximal end faces an implanted sensing photodetector (10P). A signal treating circuit as discussed with respect to FIG. 7(a) supra, including an amplifier, a filters, and so on can be interposed between the contacts (7+, 7−) and the light source (30L) to increase the definition of the optical signal sent to the encapsulation unit (5) via the optical fibre (40. FIG. 4(b) illustrates a cuff electrode unit (6e), but the same principle can apply to other electrode unit geometries and applications, including an electroencephalograph (EEG) sensor as described in the International Patent Application No PCT/EP2020/050379.

Optical sensors are any sensor configured for obtaining information by reception of a light originating from a tissue. Generally, such sensors comprise a source of light emission for emitting an optical radiation to the tissue (52), and a photodetector for capturing the light reflected, transmitted, or diffracted by the tissue. An example is shown in FIG. 4(c), wherein a tissue (52) is irradiated by the main source of light emission by an optical fibre (40, and the light transmitted and diffracted through the tissue is collected by an optical fibre (4f, 4040 in optical communication with a photodetector. Micro-optical elements (4L) as discussed supra can be provided to optimize the collection by the optical fibre (4f, 4040 of the transmitted and diffracted rays. It is clear that reflected radiations can also be collected. In this case, the optical fibre collecting the reflected and diffracted light would be on the same side of the tissue as the optical fibre (40 coupled to the main source of light emission (10L).

Since at least some wall portions of the housing have a sufficient transmittance to optical radiations, the optical sensors can be located inside the inner space (Vi) of the encapsulation unit (5). For example, the implanted source of communication light (20Li) and the implanted communication photodetector (20Pi) can be used as optical sensors. The encapsulation unit can house other optical sensors in the inner space (Vi).

External Processing Unit (100)

The external processing unit (100) controls the functions of the different components of the kit-of-parts. It comprises a user interface, allowing an operator to enter information, such as pulse parameters and commands, and also to access information provided by the AIMD (1) or by the external controller unit (300). The external processing unit (100) is in communication with an external communication unit (102) for communicating with the electronic circuit (5e) of the encapsulation unit via the implanted source of communication light (20Li) and the implanted communication photodetector (20Pi), in a manner described in continuation. The communication between the external processing unit (100) and the external communication unit (102) can be wireless, via optical fibres, or via conducting wires. Wireless communication requires each of the external processing unit (100) and the external communication unit (102) to be provided with a wireless communication device (15c, 115c).

Figure 8:
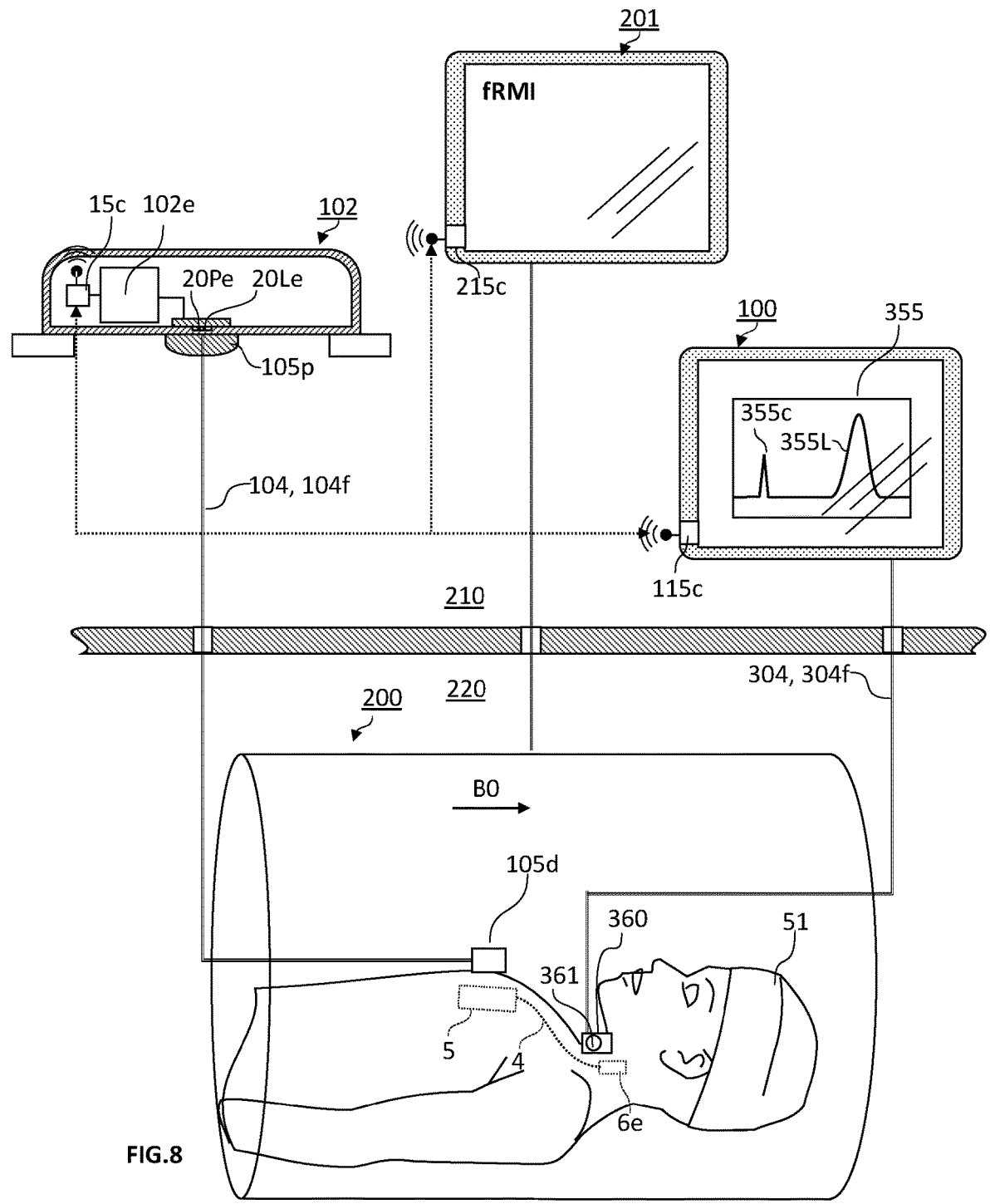
FIG. 8: Shows an embodiment of the system according to the present invention configured for controlling that the AIMD implanted in the body of the patient is fully functional in MR-image acquisition conditions, using the external laryngeal controller of FIG. 7(a).

In the embodiment comprising an external laryngeal controller (300), as illustrated in FIGS. 7(a) and 8, the optical fibre (304f) optically coupled to the laryngeal electrodes (361) comprises a distal end coupled to the external processing unit (100), either directly or indirectly through an intermediate controller (not shown). The distal end of the optical fibre (304) is coupled to a photoreceptor (not shown), which can be a photovoltaic cell configured for transforming optical signals into electric signals. The external processing unit (100) is also configured for saving and displaying the data recorded by the laryngeal electrodes (361), e.g., in the form of graphs (355) or acoustic signals (357) as illustrated in FIGS. 7(a) and 7(b) or of numerical data.

External Communication Unit (102) and Optical Communication Lead (104)

The external communication unit (102) is in communication with and controlled by the external processing unit (100). The external communication unit (102) is configured for communicating with the AIMD (1) through optical signals transferred between the two via optical fibres (104f) comprised in an optical communication lead (104). The external communication unit (102) comprises an external source of communication light (20Le), an external photodetector (20Pe), and an electronic circuit (102e). The electronic circuit (102e) is configured for, controlling the external source of communication light (20Le) to emit signals representative of the parameters and commands entered in the external processing unit (100) and transferred to the implanted communication photodetector (20Pi) via an optical fibre (104f), and transferring to the external processing unit (100) information representative of optical communication signals emitted by the implanted source of communication light (20Li) and transferred to the external photodetector (20Pe) via an optical fibre (104f), For example, in communication with, and under control of the external processing unit (100), the external communication unit (102) can transmit pulse parameters to the AIMD. This applies also to the embodiment using an external laryngeal controller (300) for communicating to the AIMD at what time (tv) exactly to emit a specific control pulse (355c) (cf. FIGS. 7(a) and 7(b)).

Figure 9:
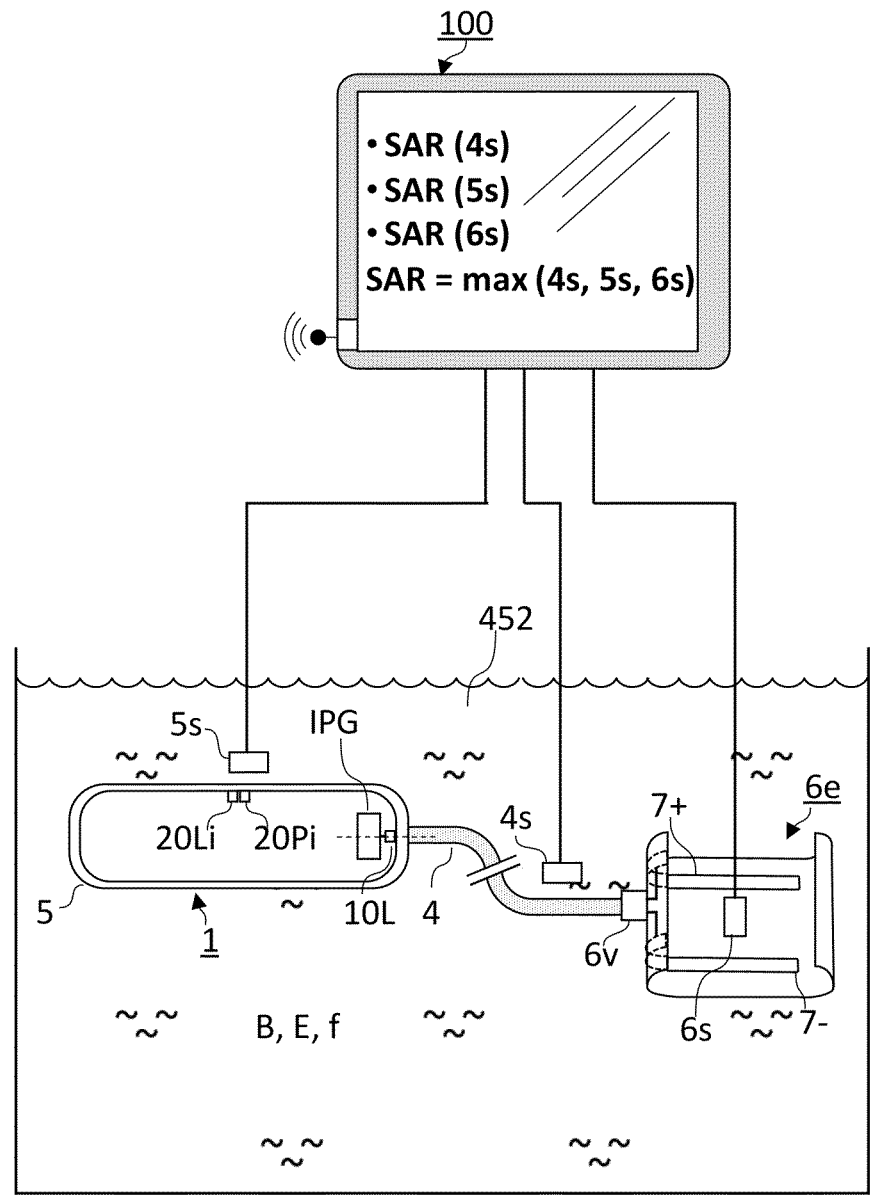
FIG. 9: Shows an experimental set-up for measuring the specific absorption rate (SAR) value of an AIMD.

The optical communication lead (104) comprises one or more optical fibres (104f) for establishing an optical communication between, the external source of communication light (20Le) of the external communication unit (102), and the implanted communication photodetector (20Pi) of the AIMD (1) and between the implanted source of communication light (20Li) of the AIMD (1) and the external communication photodetector (20Pe) of the external communication unit (102), and The optical communication lead (104) establishes a remote optical communication between the AIMD (1) and the external processing unit (100) via the external communication unit (102), as shown in FIGS. 6(a), 8, and 9. Each of the one or more optical fibres (104f) has a proximal end coupled to the external communication unit (102) in alignment with a corresponding external source of communication light (20Le) and/or a corresponding external communication photodetector (20Pe). Perfect alignment of the optical fibres with corresponding sources of light or photodetectors is required to minimize energy losses at each interface. For this reason, it is preferred that the proximal end of each of the one or more optical fibres be inserted in a proximal interface device (105p) as shown in FIGS. 6(a) and 6(b). The proximal interface device (105p) can be coupled to the external communication unit (102) such that all the foregoing optical components are optimally aligned. Micro-optical elements including one or more of lenses, collimators, diffusors, polarizers, filters, etc. can be provided to reshape a beam of light propagating in both directions between the proximal end of the one or more optical fibres and the corresponding external source of communication light (20Le) and/or a corresponding external communication photodetector (20Pe).

Each of the one or more optical fibres (104f) has a distal end configured for being optically coupled to the AIMD (1) in alignment with a corresponding implanted source of communication light (20Li) and/or a corresponding implanted communication photodetector (20Pi), across the skin (50) of a patient (51). Here again, perfect alignment of the optical fibres with corresponding sources of light or photodetectors is required to minimize energy losses at each interface. For this reason, it is preferred that the distal end of each of the one or more optical fibres be inserted in a distal interface device (105d) as shown in FIGS. 6(a) and 6(c). Micro-optical elements including lenses, collimators, etc. can be provided to reshape a beam of light propagating in both directions between the distal end of the one or more optical fibres and the skin (50) of the patient (51) (and corresponding implanted source of communication light (20Li) and/or a corresponding implanted communication photodetector (20Pi)). This is particularly important because the light beams must cross through skin (50) and tissue which scatter and diffract the beam, weakening the strength of the signal accordingly (compare in FIG. 6(c) the scattered light beams focused through lenses (solid lines) and not focused by the lenses (dotted lines)).

When alignment of the proximal interface device (105p) with the external communication unit (102) can easily be repeatedly achieved by simply providing mechanical fixtures forcing the alignment of the two components, this is not possible for aligning the distal interface device (105d), resting on an outer surface of the skin (50) of the patient (51) with the implanted optical components (20Li, 20Pi) housed in the encapsulation unit (5) of the AIMD implanted subcutaneously. To ensure repeatability of the positioning of the distal interface device (105d) in alignment with the implanted optical components (20Li, 20Pi), a solution could be to add reference marks tattooed on the skin. This solution of course leaves permanent marks on the skin of the patient, though the marks can be discreet, but is efficient only in case it can be ensured that the encapsulation unit (5) does not move inside the body. Care must be taken in the choice of inks used for the tattoos, as they may contain pigments which are magnetic and interact with the MRI's strong magnetic fields. Tattoos may also absorb energy that would normally be spread over a larger volume of tissue, thus increasing burn risks.

For aligning a primary axis (Z1) of the distal interface device with a secondary axis (Z2) of the encapsulation unit (5) with the skin (50) of the patient interposed therebetween, a centring system as described in EP3265173B1 is used in a preferred embodiment. As shown in FIGS. 6(a) and 6(c), the distal interface device (105d) comprises a number, N>2, of centring photodetectors (105pd) forming a polygon of N edges, normal to the primary axis (Z1) and which centroid belongs to the primary axis (Z1). For example, N=3 or 4. An indicator is provided which indicates how the distal interface device is to be displaced over the surface of the skin (50) of a patient (51) in order to position the distal interface device (105d) with the primary axis (Z1) being coaxial with the secondary axis (Z2) of the encapsulation unit (5), as a function of the energy received by each of the N centring photodetectors (105pd) from a light beam emitted by the implanted source of communication light (20Li) or a different source of light.

The indicator is coupled to an electronic intelligence configured for comparing the energies received by each of the N centring photodetectors (105pd), and for determining how to move the distal interface device (105d) over the surface of the skin (50) of the patient (51) such that each of the N centring photodetectors receives an equal energy from the light beam. The electronic intelligence can be located in the distal interface device (105d), so that an operator can align the distal interface device with respect to the encapsulation unit prior to positioning the patient into the MR-device. In this case, the optical communication lead (104) can comprise an optical fibre dedicated to energizing the centring system of the distal interface device (105d) via a photovoltaic cell. The distal interface device (105d) can be provided with a motorized (X-Y) table suitable for moving the distal interface device (105d) controlled by the electronic intelligence. A motorized (X-Y) table suitable for the present embodiment is described in EP3265173B1.

Alternatively, the indicator can be located in the external communication unit (102). In this embodiment, it is preferred that the distal interface device (105d) be provided with a motorized (X-Y) table as discussed supra. In this embodiment, the N centring photodetectors (105pd) are preferably located in the external communication unit (102), each one being in optical communication with the proximal end of a corresponding optical fibre (40. The distal ends of the corresponding optical fibres (40 are disposed around the centroid forming the polygon described supra. In this embodiment, the distal interface device can be centred with respect to the encapsulation unit as the patient is in the MR-device and even during treatment in case a movement of the patient may have caused a misalignment of the two components. If a motorized (X, Y) table is used in the MR-device, the number of metallic components thereof should be minimized to reduce the artefact caused by the (X, Y) table.

Once the distal interface device (105d) is positioned on the surface of the skin (50) of the patient with the primary axis (Z1) in alignment with the secondary axis (Z2), it can be fixed in place with straps and/or adhesive tapes. In case the distal interface device (105d) comprises a motorized (X-Y) table, the distal interface device (105d) can first be positioned with the axes Z1, Z2 approximately aligned, then fixed in place, and followed by fine tuning the Z1, Z2-alignment with the motorized (X-Y) table.

MRI-Friendly AIMD

As discussed in the section supra entitled "Background of the Invention", providing an MRI-friendly AIMD for implantation in a body of a patient (51) is not an easy task. Three major issues must be addressed:
(1) displacements of a component of the AIMD driven by the static magnetic field (B0) which can reach values of up to 7 T, generally about 1.5 T to 3 T,
(2) interference with or even damaging of the electronic components of the AIMD, and
(3) burning of tissues by heating of a conductive component because of induced currents.

(1) Magnetic Displacement

To avoid any components from being attracted by the magnetic fields, the number and size of components made of materials having a high magnetic susceptibility is reduced and, preferably eliminated. Magnetic susceptibility ($\chi$) is a measure of how much a material will become magnetized in an applied magnetic field. For this reason, it is preferred to use materials having a low magnetic susceptibility. In particular, it is preferred that the AIMD be made substantially only of materials having a magnetic susceptibility, $|\chi|<2 \cdot 10^{-2}$, preferably $|\chi|<10^{-2}$, wherein the magnetic susceptibility is expressed relative to volume and is dimensionless [$m^3/m^3$], as materials having a magnetic susceptibility, $|\chi|<2 \cdot 10^{-2}$, experience strong magnetic forces and torques and create image distortion and degradation even at locations remote from the imaging region. Materials having a magnetic susceptibility relative to water, $10^{-5}<|\chi-\chi_{water}|<10^{-2}-\chi_{water}$, wherein $\chi_{water}=-9.035 \cdot 10^{-5}$ do not experience easily detectable forces or torques. Care must be taken where they are located, however, as they can produce marked image distortion and degradation if they are located close to the imaging region. This would cause little to no distortion in MR-imaging of a brain region of a patient implanted with, e.g., a vagus nerve stimulator but should be carefully studied in case of a deep brain electrode or of a cochlear implant. Materials having a magnetic susceptibility relative to water, $|\chi-\chi_{water}|<10^{-5}$, do not produce easily detectable forces or torques and very limited to negligible image distortion or degradation even when they are located close to the imaging region. Whenever possible, the use of such materials should be favoured.

The use of ferromagnetic materials should be reduced and, preferably eliminated. The AIMD of the present invention preferably does not comprise any component made of a ferromagnetic material or of a material having a magnetic susceptibility relative to water, $|\chi-\chi_{water}|>10^{-2}$ of size greater than 4 $mm^3$, preferably of size greater than 3 $mm^3$. This way, movements of the AIMD due to the application of a magnetic field as well as MR-image artefacts are substantially reduced.

(2) Integrity of the Electronic Components

Strong and/or oscillating electromagnetic fields can interfere with the electronic components of the AIMD. All communication via conductive wires can be disrupted or corrupted. The strong currents induced on conductive wires by oscillating magnetic fields can damage or destroy the electronic components coupled to such conductive wires. The AIMD of the present invention does not comprise any conductive wire of substantial length. A "substantial length" is herein preferably defined as a length of at least 15 mm, preferably at least 20 mm, more preferably at least 30 mm, most preferably at least 50 mm. All communication and transportation of energy from one component to another separated by a distance greater than the substantial length are carried out optically via optical fibres (4f). Optical signals travelling through optical fibres are not affected by electromagnetic field variations and no electrical current can be induced therein. The electronic components of the AIMD are therefore safe of any burst of induced electrical current travelling through a lead.

The electronic components most vulnerable to strong and/or oscillating electromagnetic fields must be protected. For example, to minimize the impact of the electromagnetic fields generated in the MR-device, the routing in the printed circuit board (PCB) forming the electronic circuit (5e) can be appropriately designed to avoid conductive loops and/or can form a compact PCB integrated design. The amount of metal used in the electronic circuit can be reduced, for example by including no ground or no power supply plate. Small shielded inductors can be used.

Figure 10:
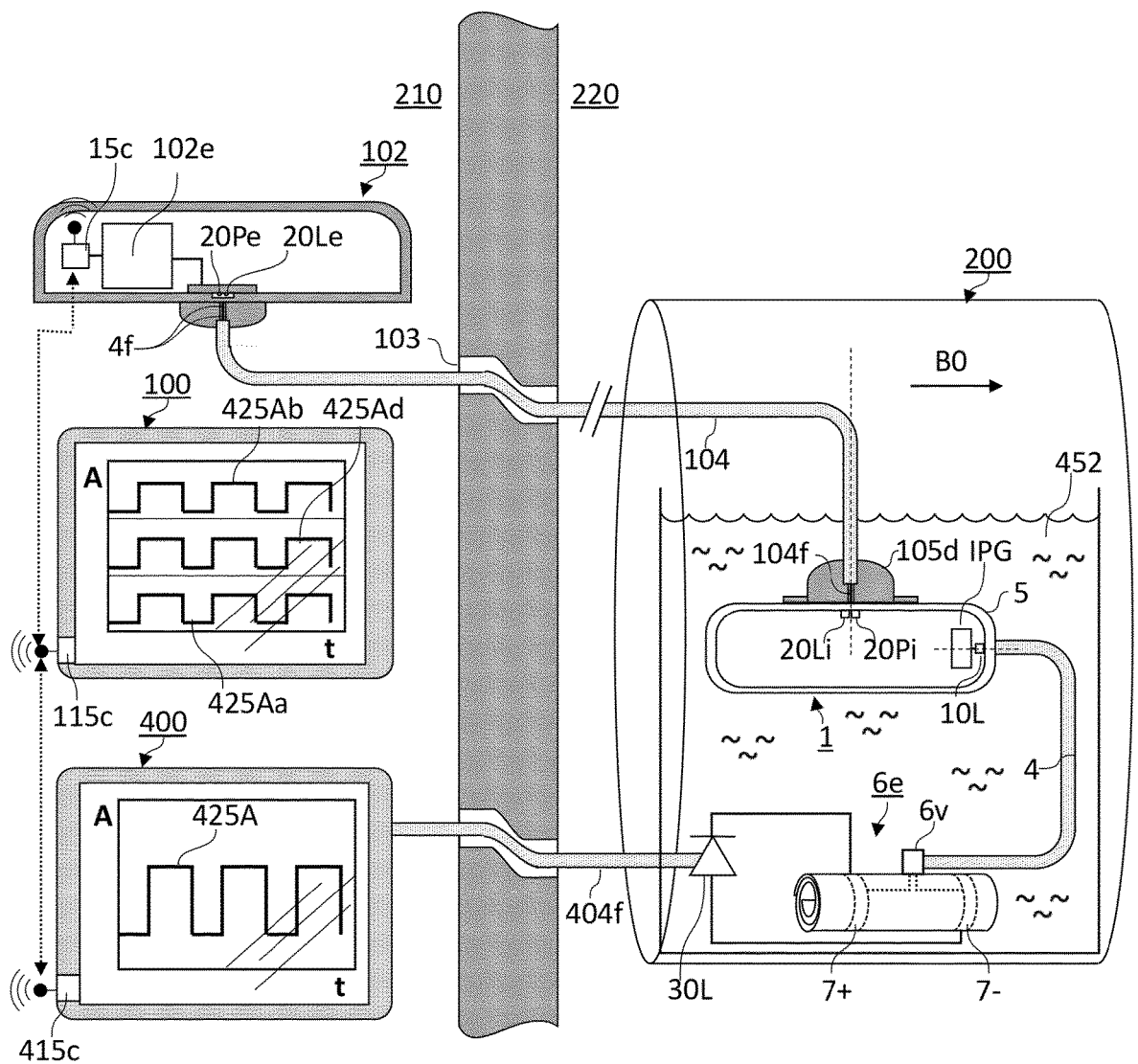
FIG. 10: Shows an embodiment of the system according to the present invention configured for controlling that the AIMD dipped in a phantom is fully functional in MR-image acquisition conditions.

The AIMD of the present invention can be fully functional upon exposure to the MR-image acquisition conditions. Full functionality of the AIMD can be determined as follows by applying MR tests using the testing criteria provided in § 17 of ISO TS 10974:2018, with a set-up as illustrated in FIG. 10.

The AIMD of the present embodiment is a stimulator comprising,
- an encapsulation unit (5) enclosing a main source of light emission (10L),
- an electrode unit (6e) comprising a photovoltaic cell (6v) and contacts (7+, 7−), and
- an energy transfer lead (4) bringing in optical communication the main source of light emission (10L) with the photovoltaic cell (6v).

The contacts (7+, 7−) of the electrode unit (6e) are electrically coupled to a light source (30L), such that when electrical pulses reach the contacts (7+, 7−), the light source (30L) emits light of intensity proportional to the intensity of the electrical pulses. As illustrated in FIGS. 3(a) and 10, the light source (30L) is in optical communication through an optical fibre (4040 with an oscilloscope (400) located outside of the MR-device (200) in a control room (210). The oscilloscope comprises a photovoltaic cell (not shown) in optical contact with the optical fibre (4040 to transform the optical signals into electrical signals for treatment by the oscilloscope (400). A treating circuit as discussed supra with respect to FIG. 7(a), including any one of an amplifier, a filter, and other components can optionally be provided between the contacts (7+, 7−) and the light source (30L), or downstream of the light source, such as at the level of the oscilloscope, for enhancing the resolution of the signal representative of the electric pulse transmitted to the contacts (7+, 7−). The oscilloscope is in communication with the external processing unit (100) for transferring thereto the data received from the light source (30L).

The AIMD is entirely immersed at a central depth in a phantom (452) according to ASTM F 2182-11A phantom (Torso+Head), filled with a saline solution imitating the electrical properties of the human body. The saline solution is composed of 0.25 wt. % NaCl dissolved in distilled water (99.75%) and has an electrical conductivity of 0.47 S/m±10% and a relative permittivity of 78. The phantom and AIMD are positioned into a MR-device (200) (GE Healthcare, Signa HDx EchoSpeed 1.5 T). The various components of the AIMD are oriented with respect to the orientation of the electromagnetic field as if they were implanted in a patient and the patient installed in the MR-device. If the electrode unit (6e) is in the shape of a cuff, the cuff is wrapped up as if enclosing a nerve.

The AIMD immersed in the phantom is positioned in the MR-device with the X- and Y-axes centred at the phantom centre and the Z-axis centred at the phantom head, wherein the axes X, Y, Z define a referential for the field of view of each image acquisition protocol. During examination the scanner is set to Normal Mode (i.e., the SAR level is limited to 2 W/kg) and the AIMD is exposed to the following electromagnetic fields with the MR-sequence conditions defined in Table 1,
- static magnetic field, B0=1.5 T,
- resonance Frequency of magnetic field (B1), f=63.85 MHz,
- maximum gradient slew rate: 120 T/m/s per axis,
- maximum gradient amplitude in each orthogonal plane: 33 mT/m,
- RF transmit coil: Body coil.

TABLE 1

MR-sequence for full-functionality testing

| Sequences | TR/TI Repetition time/ Inversion time | TE (ms) Echo Time | FA Flip angle | BW (kHz) Bandwidth | Plane | Fove (mm) | Matrix | Slice thickness (mm) |
|---|---|---|---|---|---|---|---|---|
| Localizer | 5 | 1.4 | — | 31.2 | 3 planes | 250 | 256*128 | 10 |
| SE T1 T1 Spin Echo | 483 | 15 | 72 | 31.25 | AX | 230 | 256*160 | 5 |
| FSE T2 T2 Fast Spin Echo | 3607 | 100 | — | 31.25 | AX | 230 | 384*224 | 5 |
| T2 FLAIR T2 Long Tau IR | 6000/1500 | 120 | — | 27.78 | AX | 230 | 224*115 | 6 |
| Diffusion Diffusion Weighted Imaging | 3034 | 97.5 | — | 250 | AX | 230 | 112*88 | 5 |
| 3D TOF MT | 25 | 2.7 | 20 | 20.83 | AX | 200 | 320*192 | 1 |
| Perfusion | 107 | 19.2 | 90 | 250 | AX | 220 | 64*36 | 3.5 |

The functional states of the AIMD are checked before, when possible during, and after the MR-sequence with the electronic circuit (5e) of the AIMD being configured to perform a cycling test defined by the following parameters, Standard stimulation at 1000 µA, 30 Hz, 7 s ON time,
128 bytes-memory data transfer from a defined RAM zone to another,
memory write of 128 incremental bytes to RAM,
stop stimulation for 12 s.

The AIMD output is monitored with the oscilloscope (400), for checking the reproducibility of the stimulation sequences and parameters. The RAM memory is checked before and after the MR-sequence.

The AIMD is considered as being fully functional if the following conditions are fulfilled.

the variation of the outputs before (425Ab), during (425Ad), and after (425Aa) the MR test are within the following ranges,
the variation of a frequency of the pulses of light energy is not more than ±5%, preferably not more than ±1%, and
the variation of a pulse duration is not more than ±5%, preferably not more than ±1%, and
the variation of an amplitude is not more than ±10%, preferably not more than ±5%, more preferably not more than ±1%, and
a duty cycle (=time ON/(time ON+time OFF)) is comprised between 36 and 38% before, during, and after the MR test, and
no corruption of the RAM and, preferably no corruption of the ROM and/or no unexpected system reset, is identified before, and after the MR sequence.

The AIMD of the present invention fulfils these requirements, mainly because it does not comprise any conductive wire of a length of more than 50 mm, preferably of more than 30 mm, more preferably of more than 20 mm, most preferably of more than 15 mm, nor any major component made of a conductive metal.

The foregoing test illustrated in FIG. 9 cannot be carried out on an AIMD implanted in a patient (51). Full functionality can also be monitored with an AIMD implanted in the body of a patient (51) by using the external laryngeal controller (300), with a set up as illustrated in FIGS. 7(a) and 8 and discussed supra. The patient is located in the MR-device (200) with a laryngeal electrode unit (360) coupled to the laryngeal region (Lx) thereof. The laryngeal electrode unit (360) is connected to the external processing unit (100) by an optical fibre (304f) with corresponding amplifying and filtering circuits, and micro-optical elements such as lenses (e.g., Fresnel lenses) to enhance the definition of the signals transmitted from the laryngeal electrodes (361) to the external processing unit (100). FIG. 8 shows the laryngeal electrode unit (360) connected directly to the external processing unit (100) but it is clear that it can be connected thereto indirectly, through an intermediate processor (not shown) or through the external communication unit (102).

The patient is exposed to the same MR-sequence as discussed supra with respect to FIG. 9. Control pulse parameters of a control energy pulse (355c) are entered into or are stored in the external processing unit (100), which instructs the implanted pulse generator (IPG) to emit signals representative of the control pulse parameters at a given time (tv). The laryngeal electrical signal is monitored in real time before, during, and after the MR-sequence, and the results are compared. The AIMD is considered as being fully functional if a height (Vm) and a full width at half maximum (FWHM) of the peaks (355L) measured with the activated MR-device do not deviate by more than ±10%, preferably not more than ±5% of the ones of the peaks (355L) measured with the MR-device at rest. The height (Vm) and FWHM of the peak (355L) are illustrated in FIG. 7(b). Again, the AIMD of the present invention fulfils these criteria.

(3) Heating of an AIMD Component and MRI-Safe Conditions

Heating of the components of the AIMD exposed to the MR-image acquisition conditions must be limited, to prevent any burning injury of the tissues surrounding said components. For example, it is preferred that all surfaces of the components in contact with a tissue should increase their temperatures by not more than 2° C. when exposed to an electromagnetic field required for MR-image acquisition. The rate at which energy is absorbed by the human body when exposed to a radio frequency (RF) electromagnetic field can be characterized by the specific absorption rate (SAR). SAR of an AIMD can be characterized as follows in a phantom (452) in a set up as illustrated in FIG. 9.

As illustrated in FIG. 9, the AIMD is fully immersed in the phantom (452) filled with the saline solution described supra. The phantom is maintained at a constant temperature and is placed inside a birdcage resonator compatible with ISO/TS 10974:2018 configured for exposing the implant fully immersed in the phantom at a depth of 65 mm to a magnetic field (B) oscillating at a frequency of f=64 MHz and inducing a constant tangential field (E) of 36.31 V_rms/m. The SAR's values of the three main components of the AIMD, viz., the encapsulation unit (5), the energy transfer lead (4), and the tissue interaction unit (6) are measured with one or more sensors (4s-6s). The one or more sensors are maintained at 2 mm over the exposed surfaces of the three main components of the AIMD. The one or more sensors can comprise a sensor (5s) positioned at 2 mm over the encapsulation unit (5), a sensor (4s) positioned at 2 mm over the energy transfer lead (4), and a sensor (6s) positioned at 2 mm over the tissue interaction unit (6). The sensors (4s-6s) are preferably configured to move (e.g., motorized) for scanning the whole exposed surface of each of the three main components. If a single sensor can scan over the whole exposed surface of more than one main component, it can be used alone for those components. For example, if the experimental set-up allows it, a single sensor can scan over the whole exposed surfaces of each of the encapsulation unit (5), the energy transfer lead (4), and the tissue interaction unit (6). Regardless of whether a single or several sensors are used, it is important that the SAR be measured over the whole exposed surfaces of each of the three main components and with different orientations of the components relative to the electric field, so as not to miss any hot spot of the AIMD. The specific absorption rate (SAR) is the highest of the values measured at any point of any one of the three main components and at any orientation of the AIMD. The test is repeated with different orientations of the different components of the AIMD such as to maximize RF and gradient field interaction. If the tissue interaction unit (6) is an electrode unit (6e) in the shape of a cuff, the cuff is opened to expose the contacts (7+, 7−). Each measurement over the whole exposed surfaces of each of the three main components and for each orientation is repeated three times and averaged. The highest value of the averaged measurements of each of the three main components defining the hottest spot thereof is retained as the values (SAR(4s), SAR(5s), SAR(6s)) characterizing the SAR of each of the energy transfer lead (4), the housing (5), and the tissue interaction unit (6). The SAR-value characterizing the AIMD is the highest value of the averaged highest values measured for each of the three components of the AIMD (SAR=max (SAR(4*s*), SAR(5*s*), SAR(6*s*)). In other words, the SAR-value characterizes the hottest spot measured on the whole AIMD.

The AIMD of the present invention yields a specific absorption rate (SAR) thus measured (i.e., highest value) and normalized to a background level of the phantom of not more than 4.0 dB, preferably nor more than 3.5 dB, more preferably not more than 3.2 dB.

Simulation calculations concluded that an AIMD according to the present invention and 5 characterized by the foregoing SAR values comprising an encapsulation unit (5) implanted in the subclavian region of a patient and an electrode cuff (6*e*) wrapped around a vagus nerve at a level comprised between C4 and C7 would raise the temperature of the tissues in contact therewith by less than 2° C. upon exposure to image acquisition conditions in a MRI of B0=1.5 T at normal mode and B1 oscillating at a frequency of 64 MHz.

In a preferred embodiment, the AIMD is safe according to the conditional label definition of § 3.1.11 of ASTM F2503-13 using the tests defined in ISO TS 10974:2018 and applying the criteria defined in § 22.2 of ISO 14708-3:2017, with the following conditions:
  static Magnetic Field: 1.5 T and 3 T,
  the Maximum static field spatial gradient: 30 T/m, preferably 40 T/m,
  maximum slew rate: 200 T/m/s per axis,
  RF excitation: circularly polarized,
  RF frequency: 64 MHz and 128 MHz,
  RF transmit coil type: both head coil and body coil can transmit, with the following operating mode: (1) head coil: the mode limit is the normal mode at 3.2 W/kg, (2) body coil: the mode limit is the normal mode at 2 W/kg, and preferably the first level mode at 4 W/kg,
  scan duration: no duration limit, and
  exclusion zone: no exclusion zone.

This conditional label is very little restrictive and allows the use of an AIMD according to the present invention with most MR-device installed in hospitals and healthcare centres. Note that no ASTM-norm is yet available to define MRI-safety for neither magnetic fields of 7 T, nor for linear polarization, the latter being rather seldom used, anyway. Most MR-devices do not apply static field spatial gradient greater than 20 T/m. The condition on the maximum static field spatial gradient to 30 T/m must, however, be taken into consideration when removing in emergency a patient from a MR-device in use. Note that higher values of the static field spatial gradient have not been tested.

System=Kit-of-Parts and MR-Device

The present invention also concerns a system for visualizing by a magnetic resonance imaging (MRI) technique including a functional magnetic resonance imaging (fMRI) technique, regions of a central nervous system of a patient (51) having an implanted active implantable medical device (AIMD) (1). The system comprises, a kit-of-parts as described supra, a magnetic resonance (MR-) device (200) controlled by a MR controller (201) as discussed supra.

As shown in FIG. 6(*a*), the AIMD is implanted in the patient (51) with the implanted source of communication light (20Li) and the implanted communication photodetector (20Pi), facing towards an area of skin (50) of the patient. The external processing unit (100) and the external communication unit (102) are both located in a control room (210)

The MR-device (200) is located in a Faraday cage (220) separate from the control room (210). The MR-device is configured for generating magnetic resonance images (MRI) or spectra (MRS), including functional magnetic resonance images (fMRI) or spectra (fMRS) of a central nervous system of the patient. The central nervous system includes the brain and spinal cord. The MR controller (201) is configured for controlling the functions of the MR-device and, as shown in FIG. 6(*a*) is located in the control room (210).

The proximal ends of the one or more optical fibres (104*f*) of the optical communication lead (104) are coupled to the external communication unit (102) located in the control room (210). The distal ends are coupled to the distal interface device (105*d*) and is located in the Faraday cage. The distal interface device (105*d*) ensures optical coupling of the distal end of the one or more optical fibres (104*f*) with the area of skin of the patient, in good alignment with the implanted source of communication light (20Li) and/or the implanted communication photodetector (20Pi) of the encapsulation unit (5).

One or more cage feedthroughs (103) are provided to allow communication by optical fibres and conductive wires between the control room (210) and the Faraday cage (210). The kit-of-parts of the present invention can be adapted to any existing MR-device (200) to form the system of the present invention. Existing MR-devices generally comprise electrical communication between the MR-device (200) and the MR-controller (201). The cage feedthrough is in most cases, simply a hole in a wall between the control room (210) and the Faraday cage (220) through which a conductive wire can be drawn between the two components. The optical fibres (104*f*, 304*f*, and 4040) having a proximal end located in the control room (210) and a distal end located in the Faraday cage (220) can profit of such existing holes as cage feedthroughs. Alternatively, a window can fill in the opening of a hole, and two portions of optical fibres can meet on either side of the window, to ensure a continuous optical communication between the control room and the Faraday cage.

These one or more cage feedthroughs (103) and the one or more optical fibres (104*f*) of the optical communication lead (104) establish a two-way communication between the external processing unit (100) and the electronic circuit (5*e*) of the encapsulation unit (5) for transferring parameters and commands to the electronic circuit, and for displaying information sent from the implanted source of communication light (20Li). This is explained in detail supra in the section entitled, "External Communication Unit (102) and Optical communication lead (104)."

In a preferred embodiment the AIMD comprises a main source of light emission (10L) and an implanted sensing photodetector (10P), in optical communication via corresponding optical fibres (40*f*) with a tissue interaction unit (6). In this embodiment, it is preferred that the external processing unit (100) be in communication with the MR controller (201), for synchronizing time sequences of MR images generation and of activations of one or more of the implanted source of communication light (20Li), the implanted communication photodetector (20Pi), the main source of light emission (10L), and the implanted sensing photodetector (10P).

In a first example, the sequences of the MR-device (200) involving strong RF-magnetic fields or 5 strong magnetic gradients can be synchronized with sequences of low activity of any one of the sources of light and photodetectors so as to minimize interactions between the magnetic fields and the functions of and communication with the AIMD. Conversely, communication by, and activity of the sources of light and photodetectors can be concentrated in periods of the MR-image acquisition sequence of low activity of the RF-excitation coils (200e) and gradient coils (200f, 200p, 200s). This is particularly suitable for stimulators, and more particularly for stimulators comprising an electrode unit (6e) as illustrated in FIG. 6(a), since the electrode unit (6e) comprises sections of conductive wires, though very short, and contacts (7+, 7−) which can be affected by the varying magnetic fields generated by said coils.

In a second example using the embodiment of kit-of-parts including an external laryngeal controller (300) illustrated in FIGS. 7(a) and 8, for controlling the stimulation of the vagus nerve (Vn), synchronizing time sequences of MR images generation and of activations of one or more of the sources of light (10L, 20Le, 20Li) can include taking as starting point in time for the synchronization the time (tv) when the external communication unit (102) sends a signal to the electronic circuit (5e) of the encapsulation unit (5) to instruct the implanted pulse generator (IPG) to emit signals representative of the control pulse parameters. This way, the MR-images generated by the MR-device correspond with great accuracy with the stimulation of the vagus nerve, and not only the localization of the stimulated areas of the brain can be detected, but also the response time elapsed between the emission of an electric stimulation pulse of the vagus nerve and the increase of activity of the corresponding areas of the brain which have been activated thereby.

As illustrated in FIG. 8, the external processing unit (100) is in communication with the external communication unit (102) via either conductive wires, optical fibres or wireless communication devices (115c, 15c). The external communication unit (102) is in optical communication with the AIMD (1) implanted in the patient's body positioned in the MR-device (200). At a given time (tv), the external processing unit (100) instructs the AIMD to emit one or more control pulses (355c) according to the control pulse parameters previously entered into the external processing unit (100).

The external processing unit (100) is also in communication with the MR-controller (201) via either conductive wires, optical fibres or wireless communication devices (115c, 215c). The MR-controller initiates the image acquisition sequence at time (tv), or earlier at a time t0, preceding time 5 (tv) by a defined period (δt0), depending on the desired moment of image acquisition (cf. FIG. 7(b)).

The laryngeal electrode unit (360) is coupled to the laryngeal region (Lx) of the patient (51) and is in optical communication with the external processing unit (100) via an optical fibre (304f) of the external energy transfer lead (304). After a known period of time (Δt−δt0) following the time (tv), a laryngeal activity peak (355L) is expected, representative of the CAP created on the vagus nerve (Vn) by the control pulse and propagating along the vagus and laryngeal nerves. The occurrence of the laryngeal activity peak (355L) ensures that the nerve has been effectively stimulated and subsequent activation of specific regions of the brain can be expected.

The synchronisation of the emission of a control pulse by the AIMD with the image acquisition sequence by the MR-device (201) together with the use of the laryngeal control unit (300) is advantageous in that,
- the occurrence of the laryngeal activity peak (355L) followed by the activation of specific brain regions unambiguously establishes a clear causal relation between stimulation and brain activation,
- a relationship between the shape and dimensions of the laryngeal activity peak (355L), such as the maximum amplitude (or height) (Vm), and the full width at half maximum (FWHM) with the intensities and localization of the activated brain regions can be very helpful in determining optimal pulse parameters for the treatment of the patient's disease,
- as the control pulse parameters can be changed easily, and a corresponding control pulse (355c) can be emitted at a known time (tv), the effect of each parameter on brain activity can easily be recorded to determine their respective effect on the mechanism involved; for example, a factorial design can easily be implemented with the system of this example.

The specific design of the AIMD (1) and external processing unit (100) of the present invention, includes,
- The housing of the encapsulation unit (5) made of non-metallic and non-conductive material, preferably of a transparent ceramic material, such as fused silica or spinel,
- The absence of any metallic feedthrough across the walls of the encapsulation unit,
- the use of optical fibres, and absence of conductive wires longer than 50 mm, preferably longer than 30 mm, more preferably longer than 20 mm, most preferably longer than 15 mm,
- shielding of the electronic components most vulnerable to electromagnetic fields,
- communication between the AIMD and the external processing unit (100) exclusively by optical fibres, With the foregoing features, the AIMD of the present invention is among the most convenient for use with an MR-device, not only passively, i.e., switched off during the MR-image acquisition sequence, but also actively, i.e., switched on and fully operational, for monitoring the effects of a given stimulation pulse on the activation of specific regions of the brain. A study of the effect of each parameter (e.g., with a factorial design) can easily be implemented, wherein the effects of high and low values of 5 each of the pulse parameters can be tested. The present invention also opens the door to an "a la carte" treatment stimulation pattern personalized to each patient (51).

Method of Use of the System of the Present Invention

The system of the present invention is particularly suitable for use in a method for visualizing and identifying the effects of parameters of electric or optical stimulation of tissues on the activation of corresponding zones of the brain. It is also very suitable for use in a method for establishing a treatment planning system specific to each patient, optimizing the parameters of the electric or optical stimulation of a tissue, such as a nerve, yielding the best effects on the patients. Either method comprises the following steps,
  (a) providing a system as discussed supra,
  (b) providing a patient implanted with the AIMD of the kit-of-parts of the system; wherein the AIMD preferably has a specific absorption rate (SAR) measured as described supra and normalized to a background level of a phantom of not more than 4.0 dB preferably nor more than 3.5 dB, more preferably not more than 3.2 dB,
  (c) coupling a distal end of the one or more optical fibres (1040 of the optical communication lead (104) to a skin (50) of the patient (51) in alignment with the implanted source of communication light (20Li) and the implanted communication photodetector (20Li) of the encapsulation unit (5) implanted in the patient, to establish an optical communication between the external communication unit (102) and the AIMD (1),
  (d) positioning the patient in the MR-device (200), (e) entering via the interface a first set of stimulation parameters in the external processing unit (100), and communicating the first set of stimulation parameters to the electronic circuit (5e) of the encapsulation unit (5) via the external communication unit (102), the one or more optical fibres (104f) and the implanted communication photodetector (20Li), (f) commanding from the external processing unit (100) to the IPG to deliver a stimulation to the patient according to the first set of stimulation parameters, (g) simultaneously or after a controlled delay, acquiring a MR-image or spectrum, preferably a fMR-image or spectrum of a brain or brain regions of the patient, (h) repeating steps (e) to (g) with a second and more sets of stimulation parameters.

In step (f), the MR-controller (201) can inform the external processing unit (100) that the MR-device is ready for acquiring images or spectra and/or can instruct the external processing unit to command the IPG to deliver a stimulation to the patient according to the first set of stimulation parameters, either instantaneously or after a predefined time period.

This method is advantageous over prior art methods involving acquiring MR-images of a patient's brain upon stimulation of a tissue, because in the present method the operator controls the triggering of a given stimulation pulse. The acquisition of MR-images can thus be synchronized with the delivery of the pulse with considerably more accuracy and control than in prior art methods, relying on an indication that a stimulation had been delivered. This indication is of course invariably available only after the tissue has been stimulated, which can be too late for capturing an MR-image. Furthermore, with the easy and flawless communication path provided between the external processor (100) and the AIMD (1) via the external communication unit (102) and the optical communication lead (104), which is insensitive to the electromagnetic fields generated during the acquisition of a MR-image, the operator can very easily and rapidly test different sets of stimulation parameters to assess the effect each stimulation parameter has on the patient.

These tests applied to a patient can be used to establish an 'a la carte' treatment planning system with an optimized set of stimulation parameters. Repeating such tests on a statistically representative number of patients can provide valuable knowledge on the mechanisms underlying the curing or soothing provided by neurostimulation.

| REF # | Feature |
|---|---|
| 1 | AIMD |
| 4 | Energy transfer lead |
| 4f | Optical fibre of the energy transfer lead |
| 4L | Micro-optical elements |
| 4s | Sensor at level of energy transfer lead |
| 5 | Encapsulation unit |
| 5b | Battery |
| 5e | Electronic circuit of the encapsulation unit |
| 5h | Housing |
| 5s | Sensor at level of encapsulation unit |
| 6 | Tissue interaction unit |
| 6e | Electrode unit |
| 6o | Optrode unit |
| 6s | Sensor at level of tissue interaction unit |
| 6v | PV cell of the tissue interaction unit |
| 7+, 7− | Contacts |
| 10L | Main source of light emission |
| 10P | Implanted sensing photodetector |
| 15c | Wireless communication device of external communication unit |
| 20Le | External source of communication light |
| 20Li | Implanted source of communication light |
| 20Pe | External photodetector |
| 20Pi | Implanted communication photodetector |
| 30L | Light source connected to the electrode unit |
| 50 | Skin |
| 51 | Patient |
| 52 | Tissue to be treated |
| 100 | External processing unit |
| 102 | External communication lead |
| 102e | Electronic circuit of the external communication unit |
| 103 | Cage feedthrough |
| 104 | Optical communication lead |
| 104f | Optical fire of the optical communication lead |
| 105d | Distal interface device, between distal end of optical fibre 4f and skin of the patient |
| 105p | Proximal interface device, between distal end of optical fibre 4f and external comm. unit |
| 105pd | Centring photodetector |
| 115c | Wireless communication device of external processing unit |
| 200 | MR-device |
| 200a | antenna |
| 200e | RF-excitation coils |
| 200f | X3 gradient coils |
| 200m | Main magnet unit |
| 200p | X2 gradient coils |
| 200s | X1 gradient coils |
| 201 | MR-controller |
| 210 | Control room |
| 215c | Wireless communication device of MR-controller |
| 220 | Faraday cage |
| 300 | External laryngeal controller |
| 304 | External energy transfer lead |
| 304f | Optical fibre of the energy transfer lead |
| 355 | Visual display |
| 355c | Control energy pulse |
| 355L | Peak of the laryngeal electrical activity representative of the control pulses along the Vn |
| 357 | Acoustic signal |
| 360 | Laryngeal electrode unit |
| 361 | Electrodes of the laryngeal electrode unit |
| 400 | Oscilloscope |
| 404f | Optical fibre between AIMD and oscilloscope |
| 415c | Wireless communication device of oscilloscope |
| 425a | Output of AIMD |
| 425Aa | Output of AIMD after the MR test |
| 425Ab | Output of AIMD before the MR test |
| 425Ad | Output of AIMD during the MR test |
| 452 | Phantom |
| AIMD | Active implantable medical device |
| B0 | Static magnetic field |
| B1 | Radio frequency (RF) magnetic field |
| EEG | Electroencephalogram |
| fL | Larmor frequency |
| fMRI | Functional magnetic resonance imaging |
| FWHM | Full width at half maximum |
| IPG | Implanted pulse generator |
| Lx | Laryngeal region |
| MRI | Magnetic resonance imaging |
| PPG | Photoplethysmography |
| SAR | Specific absorption rate |
| t0 | Start of time, t0 = 0 |
| tlx | Time of maximal laryngeal electric activity |
| tv | Time of control pulse emission |
| Vi | Inner space |
| Vm | Maximum amplitude of a peak of laryngeal electric activity |
| Vn | Vagus nerve |
| δt0 | Period (tv − t0) |
| Δt | Period (tlx _ t0) |

The invention claimed is:

1. A kit-of-parts for medical visualization of a subject patient's central nervous system, the kit-of-parts comprising:
an active implantable medical device (AIMD) for medical visualization of the central nervous system using magnetic resonance imaging (MRI) technology including functional magnetic resonance imaging (fMRI), the AIMD (1) comprising:
an encapsulation unit (5) defining an inner space (Vi) sealingly separated from an outer environment by a set of walls defined by an inner surface defining the boundaries of the inner space, wherein the set of walls of the encapsulation unit are made of a non-metallic material, wherein the inner space contains:
an implantable source of communication light (20Li) and an implantable communication photodetector (20Pi) facing a portion of the set of walls having a given transmittance to wavelength selected within a range of between 380 nm and 5 μm for optical communication with an exterior of the subject patient's body, and
an electronic circuit (5e) for controlling the implantable source of communication light (20Li) and the implantable communication photodetector (20Pi), thus ensuring communication with the exterior of the subject patient's body;
an external processing unit (100) comprising a user interface configured for entering parameters and commands, and for displaying information;
an external communication unit (102) in communication with the external processing unit (100) and comprising an external source of communication light (20Le), an external photodetector (20Pe), and an electronic circuit (102e) configured for:
controlling the external source of communication light to emit signals representative of the parameters and commands entered in the external processing unit (100) and received by the implantable communication photodetector (20Pi), and
transferring to the external processing unit (100) information representative of optical communication signals emitted by the implantable source of communication light (20Li) and received by the external photodetector (20Pe); and
an optical communication lead (104) comprising an optical fibre (104f) usable with the medical visualization by the MRI technique including the fMRI technique for establishing an optical communication between,
the implantable source of communication light (20Li) of the AIMD (1) and the external communication photodetector (20Pe) of the external communication unit (102), and
the external source of communication light (20Le) of the external communication unit (102), and the implantable photodetector (20Pi) of the AIMD (1),
thus allowing remote optical communication between the external processing unit (100) and the AIMD;
wherein the AIMD further comprises:
at least one of a main source of light emission (10L) of a given wavelength range between 380 nm and 5 μm, or an implantable sensing photodetector (10P), either or both being contained in the inner space (Vi) and facing a second portion of the set of walls forming a window having transmittance to the wavelength range, wherein the main source of light emission (10L) is configured for sending pulses of light energy according to defined parameters, and wherein the implantable sensing photodetector (10P) is configured for receiving optical signals;
a tissue interaction unit (6) separate from the encapsulation unit, and configured for interacting with a tissue of the subject patient;
an energy transfer lead (4) comprising an optical fibre having a proximal end coupled to the encapsulation unit (5) and facing the window of the encapsulation unit in alignment with at least one of the main source of light emission (10L) or with the implantable sensing photodetector (10P), and a distal end coupled to the tissue interaction unit, the energy transfer lead comprising no electric conductive wire; and
wherein the electronic circuit (5e) is configured for controlling the implantable implantable source of communication light (20Li), the implantable communication photodetector (20Pi), the main source of light emission (10L), and the implantable sensing photodetector (10P).

2. The kit-of-parts according to claim 1, wherein the AIMD is a stimulating AIMD comprising:
an implantable pulse generator (IPG) enclosed in the inner space and comprising the main source of light emission (10L), for sending pulses of light energy according to defined parameters, wherein the electronic circuit (5e) is configured for controlling the IPG; and
wherein the tissue interaction unit (6) is either,
an electrode unit (6e) comprising a photovoltaic cell (6v) coupled to one or more contact units, each including two or three contacts (7+, 7−), separated from one another and supported on a non-conductive support; and
wherein the distal end of the optical fibre is coupled to the electrode unit (6e) and facing the photovoltaic cell, or
an optrode unit (60).

3. The kit-of-parts according to claim 2, wherein:
the electrode unit (6e) forming the tissue interaction unit (6) is suitable for coupling to a vagus nerve of the patient (51);
the user interface of the external processing unit (100) is configured for entering control pulse parameters of a control energy pulse (355c);
the external communication unit (102) is in communication with the external processing unit (100) and is configured for sending a signal to the electronic circuit (5e) instructing the implantable pulse generator (IPG) to emit signals representative of the control pulse parameters entered in the external processing unit (100), and received by the implantable communication photodetector (20Pi);
the kit-of-parts further comprising an external laryngeal controller (300) comprising:
a laryngeal electrode unit (360) comprising laryngeal electrodes (361) suitable for being coupled to a skin (50) of a neck of the patient at the level of a laryngeal region (Lx) and suitable for measuring a laryngeal electrical activity at the laryngeal region, and
an external energy transfer lead (304) comprising one or more optical fibres (304f) for transferring an optical signal from the laryngeal electrode unit to the external processing unit (100), the optical signal being representative of a laryngeal electrical activity measured by the laryngeal electrodes (361) at the laryngeal region; and
wherein the external processing unit (100) is configured for converting optical signals transferred by the external energy transfer lead into a visual (355), numerical, or acoustic (357) form indicative of the intensity of the optical signal.

4. The kit-of-parts according to claim 1, wherein the AIMD is a monitoring device configured for monitoring biomarkers of the patient (51), comprising one or more sensors located in the inner space or in the tissue interaction unit (6); and wherein the one or more sensors comprise at least one of one or more optical sensors, electroencephalogram (EEG), electrical muscular and neural activity sensor, accelerometer, and hemodynamic activity sensor.

5. The kit-of-parts according to claim 1, wherein the non-metallic material is selected among ceramic and polymers and wherein the portion of wall has a transmittance to a wavelength of 850 nm at room temperature of at least 75%.

6. The kit-of-parts according to claim 5, wherein the non-metallic material is a fused silica or a spinel.

7. The kit-of-parts according to claim 1, further comprising a set of micro-optical elements, wherein the optical communication lead (104) comprises at least two optical fibres (104*f*), and wherein each of the at least two optical fibres comprise:
   a proximal end inserted in a proximal interface device (105*p*) which is coupled to the external communication unit (102) such that the optical fibres are optimally aligned with the external communication photodetector (20Pe) and external source of communication light (20Le) of the external communication unit (102); and
   a distal end inserted in a distal interface device (105*d*), wherein for aligning the distal ends of the optical fibres (104*f*) with the implantable source of communication light (20Li) and the implantable communication photodetector (20Li), the distal interface device (105*d*) comprises a number, N>2, of centring photodetectors (105*pd*) forming a polygon of N edges, configured for receiving and detecting an intensity of a light beam emitted by the implantable source of communication light (20Li) when the distal interface device (105*d*) is laid on a skin (50) of the patient (51) over an approximate position of the encapsulation unit (5) with the N centring photodetectors (105*pd*) facing towards the skin; and
wherein the set of micro-optical elements comprises one or more of lenses, collimators, diffusors, polarizers, or filters, which are configured for reshaping a beam of light propagating in both directions from or towards the proximal end and distal end of each of the at least two optical fibres.

8. A system for visualizing by magnetic resonance imaging (MRI) including functional magnetic resonance imaging (fMRI), regions of a central nervous system of a patient (51) having an active implantable medical device (AIMD) (1), the system comprising:
   the kit-of-parts according to claim 1, wherein the AIMD, the implantable source of communication light (20Li), and the implantable communication photodetector (20Pi) are implantable facing towards an area of skin of the patient;
   a magnetic resonance (MR) device (200) located in a Faraday cage (220), for generating magnetic resonance images (MRI) or spectra (MRS), including functional magnetic resonance images (fMRI) or spectra (fMRS) of a central nervous system of the patient;
   a control room (210) located outside of the Faraday cage, and enclosing,
      the external processing unit (100),
      the external communication unit (102), in wireless communication or in wire or optical communication with the external processing unit (100), and
      an MR controller (201) for controlling the functions of the MR-device;
   a cage feedthrough (103) configured for providing a continuous optical communication through each of the one or more optical fibres (104*f*) of the optical communication lead (104) between,
      a proximal end coupled to the external communication unit (102) and located in the control room, and
      a distal end located in the Faraday cage, and configured to be coupled to the area of skin of the patient, in good alignment with at least one of the implantable source of communication light (20Li) or the implantable communication photodetector (20Pi) of the encapsulation unit (5); and
   wherein the external processing unit (100) is in two-way communication with the electronic circuit (5*e*) of the encapsulation unit (5) for transferring parameters and commands to the electronic circuit (5*e*), and for displaying information sent from the implantable source of communication light (20Li).

9. The system according to claim 8, wherein the external processing unit (100) is in communication with the MR controller (201), for synchronizing time sequences of MR images generation and of activations of one or more of the implantable source of communication light (20Li), the implantable communication photodetector (20Pi), the main source of light emission (10L), and the implantable sensing photodetector (10P).

10. The system according to claim 9, wherein synchronizing time sequences of MR images generation and of activations of one or more of the implantable source of communication light (20Li) includes taking as starting point in time for the synchronization the time when the external communication unit (102) sends a signal to the electronic circuit (5*e*) of the encapsulation unit (5) to instruct an implantable pulse generator (IPG) to emit signals representative of the control pulse parameters.

* * * * *